United States Patent
Swanson et al.

(10) Patent No.: US 11,850,401 B2
(45) Date of Patent: Dec. 26, 2023

(54) AUTO-INSERT INJECTOR

(71) Applicant: Antares Pharma, Inc., Ewing, NJ (US)

(72) Inventors: Kevin Swanson, Plymouth, MN (US); Aaron V. Hua, Maple Grove, MN (US)

(73) Assignee: ANTARES PHARMA, INC., Ewing, NJ (US)

( * ) Notice: Subject to any disclaimer, the term of this patent is extended or adjusted under 35 U.S.C. 154(b) by 0 days.

(21) Appl. No.: 16/435,450

(22) Filed: Jun. 7, 2019

(65) Prior Publication Data

US 2019/0374717 A1    Dec. 12, 2019

Related U.S. Application Data

(60) Provisional application No. 62/682,816, filed on Jun. 8, 2018.

(51) Int. Cl.
*A61M 5/20*    (2006.01)
*A61M 5/32*    (2006.01)

(52) U.S. Cl.
CPC ........ *A61M 5/2033* (2013.01); *A61M 5/3202* (2013.01); *A61M 2005/206* (2013.01); *A61M 2005/208* (2013.01)

(58) Field of Classification Search
CPC .............. A61M 5/2033; A61M 5/3202; A61M 2005/206; A61M 2005/3261;
(Continued)

(56) References Cited

U.S. PATENT DOCUMENTS 2,866,458 A  12/1958  Hein, Jr.
3,797,489 A   3/1974  Sarnoff
(Continued)

FOREIGN PATENT DOCUMENTS

DE    8326217 U1    12/1983
EP    1743666 A1     7/2005
(Continued)

OTHER PUBLICATIONS

International Search Report dated Aug. 26, 2019 for International Patent Application No. PCT/US2019/036178, 2 pages.
(Continued)

*Primary Examiner* — Shefali D Patel
*Assistant Examiner* — Illiam R Frehe
(74) *Attorney, Agent, or Firm* — Morgan, Lewis & Bockius LLP

(57) ABSTRACT

In one embodiment there is an injector comprising a housing having a proximal end and a distal end, a shell, a plunger, a needle guard, a first member, and an actuation assembly. The shell may be within the housing and may have a cavity to receive at least a portion of a medicament chamber. The shell may be moveable with respect to the housing from an initial position to an injecting position. The plunger may be moveable with respect to the shell. The needle guard may be moveable between an extended position and a retracted position. The first member may be within the housing. The actuation assembly may be coupled to the housing and the shell. The needle guard may move the first member with respect to the housing as the needle guard moves from the extended position to the retracted position. The actuation assembly may move the shell from the initial position to the injecting position when the first member moves with respect to the housing. The actuation assembly may move the plunger with respect to the shell when the shell is in the injecting position.

29 Claims, 27 Drawing Sheets

(58) Field of Classification Search
CPC .... A61M 2005/2073; A61M 2005/208; A61M 2005/2414; A61M 5/20; A61M 5/3243; A61M 2005/3247; A61M 2005/3265; A61M 2005/3267; A61M 2005/3268; A61M 3/3205; A61M 5/321; A61M 5/3245; A61M 5/326

See application file for complete search history.

(56) References Cited

U.S. PATENT DOCUMENTS

| | | | |
|---|---|---|---|
| 3,882,863 A | 5/1975 | Sarnoff et al. |
| 4,031,893 A | 6/1977 | Kaplan et al. |
| 4,226,235 A | 10/1980 | Sarnoff et al. |
| 4,329,988 A | 5/1982 | Sarnoff et al. |
| 4,394,863 A | 7/1983 | Bartner |
| 4,723,937 A | 2/1988 | Sarnoff et al. |
| 5,282,793 A | 2/1994 | Larson |
| 5,295,965 A | 3/1994 | Wilmot |
| 5,320,609 A | 6/1994 | Haber et al. |
| 5,383,864 A | 1/1995 | van den Heuvel |
| 5,478,316 A | 12/1995 | Bitdinger et al. |
| 5,658,259 A | 8/1997 | Pearson et al. |
| 5,681,291 A | 10/1997 | Galli |
| 5,713,866 A | 2/1998 | Wilmot |
| 6,210,369 B1 | 4/2001 | Wilmot et al. |
| 6,270,479 B1 | 8/2001 | Bergens et al. |
| 6,280,421 B1 | 8/2001 | Kirchhofer et al. |
| 6,391,003 B1 | 5/2002 | Lesch, Jr. |
| 6,428,528 B2 | 8/2002 | Sadowski et al. |
| 6,544,234 B1 | 4/2003 | Gabriel |
| 6,565,553 B2 | 5/2003 | Sadowski et al. |
| 6,620,137 B2 | 9/2003 | Kirchhofer et al. |
| 6,689,092 B2 | 2/2004 | Zierenberg et al. |
| 6,746,429 B2 | 6/2004 | Sadowski et al. |
| 6,767,336 B1 | 7/2004 | Kaplan |
| 6,805,686 B1 | 10/2004 | Fathallah et al. |
| 6,846,302 B2 | 1/2005 | Shemesh et al. |
| 7,112,187 B2 | 9/2006 | Karlsson |
| 7,118,553 B2 | 10/2006 | Scherer |
| 7,297,136 B2 | 11/2007 | Wyrick |
| 7,357,790 B2 | 4/2008 | Hommann et al. |
| 7,442,185 B2 | 10/2008 | Amark et al. |
| 7,449,012 B2 | 11/2008 | Young et al. |
| 7,465,289 B2 | 12/2008 | Marshall |
| 7,488,308 B2 | 2/2009 | Lesch, Jr. |
| 7,500,963 B2 | 3/2009 | Westbye et al. |
| 7,621,891 B2 | 11/2009 | Wyrick |
| 7,635,350 B2 | 12/2009 | Scherer |
| 7,635,356 B2 | 12/2009 | Stamp |
| 7,749,195 B2 | 7/2010 | Hommann |
| D621,929 S | 8/2010 | Van der Stappen |
| 7,785,292 B2 | 8/2010 | Harrison |
| D623,738 S | 9/2010 | Van der Stappen |
| 7,789,853 B2 | 9/2010 | Kriesel |
| 7,794,432 B2 | 9/2010 | Young et al. |
| 7,806,866 B2 | 10/2010 | Hommann et al. |
| 7,811,261 B2 | 10/2010 | Rubinstein |
| 7,918,823 B2 | 4/2011 | Edwards et al. |
| 7,927,303 B2 | 4/2011 | Wyrick et al. |
| 7,931,618 B2 | 4/2011 | Wyrick et al. |
| D638,539 S | 5/2011 | Ellis et al. |
| 7,976,499 B2 | 7/2011 | Grunhut et al. |
| 8,021,335 B2 | 9/2011 | Lesch, Jr. |
| 8,048,029 B2 | 11/2011 | Gillespie, III et al. |
| 8,048,035 B2 | 11/2011 | Mesa et al. |
| 8,123,719 B2 | 2/2012 | Edwards et al. |
| 8,123,724 B2 | 2/2012 | Gillespie, III |
| 8,162,886 B2 | 4/2012 | Sadowski et al. |
| 8,211,059 B2 | 7/2012 | Kriesel |
| 8,251,947 B2 | 8/2012 | Kramer et al. |
| 8,277,414 B2 | 10/2012 | Barrow-Williams et al. |
| 8,313,463 B2 | 11/2012 | Barrow-Williams et al. |
| 8,313,464 B2 | 11/2012 | Barrow-Williams |
| 8,313,465 B2 | 11/2012 | Harrison |
| 8,343,110 B2 | 1/2013 | Harrison et al. |
| 8,409,149 B2 | 4/2013 | Hommann et al. |
| 8,419,686 B2 | 4/2013 | Sadowski et al. |
| 8,460,246 B2 | 6/2013 | Steyn |
| 8,496,619 B2 | 7/2013 | Kramer et al. |
| 8,529,510 B2 | 9/2013 | Giambattistia et al. |
| 8,529,518 B2 | 9/2013 | Larsen et al. |
| 8,562,564 B2 | 10/2013 | Lesch, Jr. |
| 8,579,865 B2 | 11/2013 | Wotton et al. |
| 8,591,465 B2 | 11/2013 | Hommann |
| 8,647,306 B2 | 2/2014 | Schwirtz et al. |
| RE44,846 E | 4/2014 | Sadowski et al. |
| RE44,847 E | 4/2014 | Sadowski et al. |
| 8,696,618 B2 | 4/2014 | Kramer et al. |
| 8,734,393 B2 | 5/2014 | Cleathero |
| 8,734,402 B2 | 5/2014 | Sharp et al. |
| 8,747,357 B2 | 6/2014 | Stamp et al. |
| 8,758,299 B2 | 6/2014 | Sadowski et al. |
| 8,801,674 B2 | 8/2014 | Rolfe et al. |
| 8,870,827 B2 | 10/2014 | Young et al. |
| 8,876,768 B2 | 11/2014 | Hourmand et al. |
| 8,900,197 B2 | 12/2014 | Crow |
| 8,900,200 B2 | 12/2014 | Doyle |
| 8,915,886 B2 | 12/2014 | Cowe |
| 8,915,889 B2 | 12/2014 | Cox et al. |
| 8,945,049 B2 | 2/2015 | Hommann et al. |
| 8,945,063 B2 | 2/2015 | Wotton et al. |
| 8,992,476 B2 | 3/2015 | Shang et al. |
| 9,011,387 B2 | 4/2015 | Ekman et al. |
| 9,033,933 B2 | 5/2015 | Boyd et al. |
| 9,033,935 B2 | 5/2015 | Brostrom |
| 9,056,170 B2 | 6/2015 | Edwards et al. |
| 9,072,839 B2 | 7/2015 | Kouyoumjian et al. |
| 9,132,236 B2 | 9/2015 | Karlsson et al. |
| 9,132,242 B2 | 9/2015 | Kemp et al. |
| 9,144,648 B2 | 9/2015 | Lesch, Jr. et al. |
| 9,180,259 B2 | 10/2015 | Lesch, Jr. |
| 9,179,260 B2 | 11/2015 | Ostrander et al. |
| 9,205,199 B2 | 12/2015 | Kemp et al. |
| 9,216,256 B2 | 12/2015 | Olson et al. |
| 9,220,660 B2 | 12/2015 | Sund et al. |
| 9,220,847 B2 | 12/2015 | Holmqvist et al. |
| 9,233,213 B2 | 1/2016 | Olson et al. |
| 9,242,053 B2 | 1/2016 | Wozencroft |
| 9,283,326 B2 | 3/2016 | Kemp et al. |
| 9,283,327 B2 | 3/2016 | Hourmand et al. |
| 9,333,304 B2 | 5/2016 | Brereton et al. |
| 9,333,309 B2 | 5/2016 | Sadowski et al. |
| 9,364,610 B2 | 6/2016 | Kramer et al. |
| 9,364,611 B2 | 6/2016 | Kramer et al. |
| 9,393,367 B2 | 7/2016 | Wotton et al. |
| 9,408,973 B2 | 8/2016 | Shang et al. |
| 9,415,176 B1 | 8/2016 | Benson et al. |
| 9,421,333 B2 | 8/2016 | Wotton et al. |
| 9,421,337 B2 | 8/2016 | Kemp et al. |
| 9,427,528 B2 | 8/2016 | Hommann et al. |
| 9,446,195 B2 | 9/2016 | Kramer et al. |
| 9,446,196 B2 | 9/2016 | Hourmand et al. |
| 9,486,583 B2 | 11/2016 | Lannan et al. |
| 9,492,622 B2 | 11/2016 | Brereton et al. |
| 9,526,845 B2 | 12/2016 | Roberts et al. |
| 9,533,102 B2 | 1/2017 | Lesch, Jr. |
| 9,561,333 B2 | 2/2017 | Cox et al. |
| 9,566,395 B2 | 2/2017 | Denny et al. |
| 9,586,007 B2 | 3/2017 | Roervig et al. |
| 9,586,010 B2 | 3/2017 | Mesa et al. |
| 9,604,003 B2 | 3/2017 | Brereton et al. |
| 9,616,173 B2 | 4/2017 | Slate et al. |
| 9,616,183 B2 | 4/2017 | Wozencroft |
| 9,629,959 B2 | 4/2017 | Lesch |
| 9,636,459 B2 | 5/2017 | Brereton et al. |
| 9,643,770 B2 | 5/2017 | Denny et al. |
| 9,675,757 B2 | 6/2017 | Harrison |
| 9,682,200 B2 | 6/2017 | Denny et al. |
| 9,687,607 B2 | 6/2017 | Brereton et al. |
| 9,692,829 B2 | 6/2017 | Starr et al. |
| 9,675,762 B2 | 7/2017 | Cronenberg et al. |
| 9,707,344 B2 | 7/2017 | Cowe |
| 9,707,354 B2 | 7/2017 | Madsen et al. |
| 9,724,472 B2 | 8/2017 | Hourmand et al. |

(56) References Cited

U.S. PATENT DOCUMENTS

| | | |
|---|---|---|
| 9,724,479 B2 | 8/2017 | Sutkin et al. |
| 9,736,642 B2 | 8/2017 | Ostrander et al. |
| 9,737,670 B2 | 8/2017 | Sadowski et al. |
| 9,744,302 B2 | 8/2017 | Travanty |
| 9,750,881 B2 | 9/2017 | Wotton et al. |
| 9,750,899 B2 | 9/2017 | Ostrander et al. |
| 9,775,948 B2 | 10/2017 | Bechmann et al. |
| 9,789,257 B2 | 10/2017 | Travanty |
| 9,807,174 B2 | 10/2017 | Starr et al. |
| 9,808,582 B2 | 11/2017 | Kramer et al. |
| 9,821,115 B2 | 11/2017 | Wozencroft |
| 9,821,122 B2 | 11/2017 | Sutkin et al. |
| 9,844,634 B2 | 12/2017 | Lewkonya et al. |
| 9,855,392 B2 | 1/2018 | Hommann et al. |
| 9,867,949 B2 | 1/2018 | Sund et al. |
| 9,907,910 B2 | 3/2018 | Constantineau et al. |
| 9,950,125 B2 | 4/2018 | Wotton et al. |
| 9,962,496 B2 | 5/2018 | Vogt et al. |
| 9,981,086 B2 | 5/2018 | Cowe et al. |
| 9,987,436 B2 | 6/2018 | Giambattista et al. |
| 10,058,654 B2 | 8/2018 | Gabrielsson |
| 10,105,496 B2 | 10/2018 | Aneas |
| 10,124,115 B2 | 11/2018 | Swanson et al. |
| 10,238,662 B2 | 3/2019 | Wotton et al. |
| 10,252,005 B2 | 4/2019 | Row et al. |
| 10,279,131 B2 | 5/2019 | Kramer et al. |
| 10,335,554 B2 | 7/2019 | Rubinstein et al. |
| 10,357,609 B2 | 7/2019 | Kramer et al. |
| 10,357,617 B2 | 7/2019 | Holmqvist |
| 10,493,215 B2 | 12/2019 | Giambattista et al. |
| 10,500,348 B2 | 12/2019 | Olson et al. |
| 10,525,213 B2 | 1/2020 | Stefanov |
| 10,555,954 B2 | 2/2020 | Wotton et al. |
| 2005/0101919 A1 | 5/2005 | Brunnberg |
| 2006/0024124 A1 | 10/2006 | Scherer |
| 2007/0017533 A1 | 1/2007 | Wyrick |
| 2008/0154199 A1 | 6/2008 | Wyrick |
| 2008/0195056 A1 | 8/2008 | Bishop et al. |
| 2009/0149809 A1 | 6/2009 | Bollenbach et al. |
| 2010/0100039 A1 | 4/2010 | Wyrick |
| 2010/0268170 A1 | 10/2010 | Carrel et al. |
| 2010/0292653 A1* | 11/2010 | Maritan .............. A61M 5/2033 604/198 |
| 2011/0137247 A1 | 6/2011 | Mesa et al. |
| 2012/0046609 A1 | 2/2012 | Mesa et al. |
| 2012/0101475 A1 | 4/2012 | Wilmot et al. |
| 2013/0023825 A1* | 1/2013 | Edwards ............ A61M 5/3202 604/196 |
| 2013/0150797 A1 | 6/2013 | Lesch, Jr. |
| 2013/0211330 A1 | 8/2013 | Pedersen et al. |
| 2013/0310757 A1 | 11/2013 | Brereton et al. |
| 2014/0025006 A1 | 1/2014 | Takemoto |
| 2014/0207073 A1 | 7/2014 | Shang et al. |
| 2014/0257200 A1 | 9/2014 | Auerbach et al. |
| 2014/0364812 A1 | 12/2014 | Lumme et al. |
| 2015/0011944 A1 | 1/2015 | Young et al. |
| 2015/0073383 A1 | 3/2015 | Wilmot et al. |
| 2015/0174323 A1 | 6/2015 | Edwards et al. |
| 2015/0209517 A1 | 7/2015 | Brunnberg et al. |
| 2015/0231333 A1 | 8/2015 | Lannan et al. |
| 2015/0283323 A1 | 10/2015 | Young et al. |
| 2015/0343146 A1* | 12/2015 | Monrad ............ A61M 5/2466 604/198 |
| 2016/0001005 A1* | 1/2016 | Bechmann ............ A61M 5/326 604/135 |
| 2016/0038678 A1 | 2/2016 | Kemp et al. |
| 2016/0106920 A1* | 4/2016 | Stefansen ............ A61M 5/326 604/198 |
| 2016/0129199 A1 | 5/2016 | Bitar et al. |
| 2016/0129200 A1 | 5/2016 | Jennings et al. |
| 2016/0129201 A1 | 5/2016 | Jennings et al. |
| 2016/0144129 A1 | 5/2016 | Mosebach et al. |
| 2016/0158460 A1 | 6/2016 | Mesa et al. |
| 2016/0199588 A1 | 7/2016 | Kemp |
| 2016/0228642 A1 | 8/2016 | Cowe |
| 2016/0263326 A1 | 9/2016 | Kramer et al. |
| 2016/0361502 A1 | 12/2016 | Hommann et al. |
| 2016/0367763 A1 | 12/2016 | Tschirren et al. |
| 2017/0007764 A1 | 1/2017 | Saussaye |
| 2017/0106146 A1* | 4/2017 | Folk .................. A61M 5/3245 |
| 2017/0173269 A1 | 6/2017 | Wozencroft |
| 2017/0173271 A1 | 6/2017 | Young et al. |
| 2017/0182250 A1 | 6/2017 | Boström et al. |
| 2017/0197036 A1 | 7/2017 | Brereton et al. |
| 2017/0216526 A1 | 8/2017 | Brereton et al. |
| 2017/0216527 A1 | 8/2017 | Lesch |
| 2017/0246403 A1 | 8/2017 | Cowe et al. |
| 2017/0290982 A1 | 10/2017 | Edwards et al. |
| 2017/0326298 A1 | 11/2017 | Hourmand et al. |
| 2017/0348488 A1 | 12/2017 | Bechmann et al. |
| 2017/0361021 A1 | 12/2017 | Wotton et al. |
| 2018/0028753 A1 | 2/2018 | Wilmot et al. |
| 2018/0043108 A1 | 2/2018 | Mesa et al. |
| 2018/0050156 A1 | 2/2018 | Travanty |
| 2018/0078713 A1* | 3/2018 | Hommann ............ A61M 5/326 |
| 2018/0093045 A1 | 4/2018 | Mehawej et al. |
| 2018/0140782 A1 | 5/2018 | Kemp et al. |
| 2018/0161521 A1 | 6/2018 | Sanders et al. |
| 2018/0161522 A1 | 6/2018 | Sanders et al. |
| 2018/0169338 A1 | 6/2018 | Mosebach et al. |
| 2018/0185583 A1 | 7/2018 | Hogdahl |
| 2018/0193562 A1 | 7/2018 | Gibson et al. |
| 2018/0221589 A1 | 8/2018 | Vogt et al. |
| 2018/0228974 A1* | 8/2018 | Cowe .................. A61M 5/2033 |
| 2018/0289899 A1 | 10/2018 | Gould |
| 2019/0030260 A1 | 1/2019 | Wotton et al. |
| 2019/0046728 A1 | 2/2019 | Swanson et al. |
| 2019/0224215 A1 | 7/2019 | Wotton et al. |
| 2019/0240407 A1 | 8/2019 | Constantineau et al. |
| 2019/0240415 A1 | 8/2019 | Holmqvist |
| 2019/0255257 A1 | 8/2019 | Daily et al. |
| 2019/0275250 A1 | 9/2019 | Constantineau et al. |
| 2019/0374717 A1 | 12/2019 | Swanson et al. |
| 2019/0388623 A1 | 12/2019 | Rubinstein et al. |
| 2020/0023141 A1 | 1/2020 | Giambattista et al. |
| 2020/0054838 A1 | 2/2020 | Olson et al. |
| 2020/0054840 A1 | 2/2020 | Olson et al. |
| 2021/0196896 A1* | 7/2021 | Alexandersson . A61M 5/31513 |

FOREIGN PATENT DOCUMENTS

| | | | |
|---|---|---|---|
| EP | 1743666 B1 | 5/2009 | |
| WO | 9421316 A1 | 9/1994 | |
| WO | WO199421316 A1 | 9/1994 | |
| WO | WO200137898 A2 | 5/2001 | |
| WO | WO2002083211 A1 | 10/2002 | |
| WO | WO2003082386 A1 | 10/2003 | |
| WO | WO2004108194 A1 | 12/2004 | |
| WO | 2006129196 A1 | 4/2005 | |
| WO | 2009007229 A1 | 7/2005 | |
| WO | WO2015004052 A1 | 10/2006 | |
| WO | WO2006129196 A1 | 12/2006 | |
| WO | WO2009007229 A1 | 1/2009 | |
| WO | 2009040605 A1 | 4/2009 | |
| WO | WO2015004049 A1 | 1/2015 | |
| WO | 2016046131 A1 | 3/2016 | |
| WO | WO2017/062005 A1 | 4/2017 | |
| WO | 2017125733 A1 | 7/2017 | |
| WO | WO2017125733 A1 | 7/2017 | |
| WO | 2017178237 A1 | 10/2017 | |
| WO | WO2017178237 A1 | 10/2017 | |
| WO | WO-2017178237 A1 * | 10/2017 | .......... A61M 5/2033 |
| WO | 2017207224 A1 | 12/2017 | |
| WO | WO2017207224 A1 | 12/2017 | |
| WO | 2018060695 A2 | 4/2018 | |
| WO | WO2018060695 A2 | 4/2018 | |
| WO | WO2018/111815 A1 | 6/2018 | |

(56) References Cited

FOREIGN PATENT DOCUMENTS

WO     WO2018/111816 A2    6/2018
WO     WO2019/237082 A1    12/2019

OTHER PUBLICATIONS

Written Opinion dated Aug. 26, 2019 for International Patent Application No. PCT/US2019/036178, 8 pages.
Canadian Office Action for Canadian Patent Application No. 3,101,995 dated Feb. 2, 2022.
Extended European Search Report for corresponding application No. 19814073.3 dated Feb. 11, 2022, 10 pages.
Japanese Office Action translation for corresponding application No. 2020-567084 dated Jan. 31, 2022, 4 pages.
Examination Report for corresponding European Patent Application No. 19 814 073.3 dated May 3, 2023, 8 pages.

\* cited by examiner

AUTO-INSERT INJECTOR

CROSS-REFERENCE TO RELATED APPLICATIONS

This application claims the benefit of U.S. Provisional Patent Application No. 62/682,816 filed Jun. 8, 2018 entitled "Auto-Insert Injector", which is incorporated by reference herein in its entirety.

BACKGROUND OF THE INVENTION

The present invention generally relates to an injector and, more particularly, to an injector that may auto-insert a needle into a patient or user.

BRIEF SUMMARY OF THE INVENTION

In one embodiment there is an injector including a housing having a proximal end and a distal end, a shell, a plunger, a needle guard, a first member, and an actuation assembly. The shell may be within the housing and may have a cavity to receive at least a portion of a medicament chamber. The shell may be moveable with respect to the housing from an initial position to an injecting position. The plunger may be moveable with respect to the shell. The needle guard may be moveable between an extended position and a retracted position. The first member may be within the housing and coupled to the housing. The actuation assembly may be coupled to the housing and the shell. The needle guard may move the first member with respect to the housing as the needle guard moves from the extended position to the retracted position. The actuation assembly may move the shell from the initial position to the injecting position when the first member moves with respect to the housing. The actuation assembly may move the plunger with respect to the shell when the shell is in the injecting position.

Proximal movement of the needle guard may move the first member proximally with respect to the housing. The shell may move with respect to the housing in response movement of the needle guard. Movement of the needle guard may trigger the injector. The shell may move distally with respect to the housing when the first member moves proximally with respect to the housing. The first member may include a detent moveable from a first position to a second position. The detent may engage the housing to prevent movement of the first member when the detent is in the first position. The detent may be disengaged from the housing when the detent is in the second position. The needle guard may prevent movement of the detent from the first position to the second position when the needle guard is in the extended position.

In a further embodiment, the injector includes a second member fixed to the housing, the second member including a catch engageable with the shell to prevent movement of the shell with respect to the housing. The second member may at least partially encircle the shell. The shell may include a recess and the catch may be positioned within the recess when the catch is in a first position. The catch may move out of the recess when the first member moves with respect to the housing. The actuation assembly may include a first biasing element operatively associated with the housing and the shell. The first biasing element may move the shell relative to the housing from the initial position to the injecting position when the first member moves with respect to the housing. The actuation assembly may include a second biasing element operatively associated with the shell and the plunger. The second biasing element may move the plunger with respect to the shell when the shell is in the injecting position. The shell may include an engagement member moveable from an engaged position wherein the engagement member prevents movement of the ram to a disengaged position wherein the ram can move with respect to the shell. The engagement member may be in the engaged position when the shell is in the initial position. The engagement member may be in the disengaged position when the shell is in the injecting position.

In a further embodiment, the injector includes a second member fixed to the housing, the second member including a catch engageable with the shell to prevent movement of the shell with respect to the housing. The second member may block movement of the engagement member from the engaged position to the disengaged position when the shell is in the initial position. In a further embodiment, the injector include a syringe and a syringe holder. The syringe holder may include a first end, a second end, a longitudinal axis extending from the first end to the second end, and a sidewall extending from the first end toward the second end. The sidewall may define a receiving area for the syringe. The sidewall may include a sidewall opening such that the syringe can be loaded into the syringe holder from a side of the syringe holder. The syringe may be loaded into the syringe holder without moving axially through a rear opening of the syringe holder. A needle shield may be coupled to the syringe and the syringe may be loaded into the syringe holder without passing the needle shield through the syringe holder The sidewall opening may extend from the first end to the second end. The syringe may include a body defining a medicament chamber, a needle fluidly coupled to the medicament chamber, and a needle shield that receives the needle. The needle shield may have a needle shield diameter. The syringe holder may include an end wall having an end wall opening with an end wall opening diameter that is smaller than the needle shield diameter. The syringe may include a syringe flange at a proximal end of the syringe, wherein a distal end of the syringe engages the end wall and the syringe flange is spaced from the second end of the sidewall when the syringe is coupled to the syringe holder.

In a further embodiment, the injector includes a needle shield remover having a projection positioned between a proximal end of the needle shield and the distal end of the syringe. In a further embodiment, the injector includes a cap coupled to the housing. The needle shield remover may be coupled to the cap such that the needle shield is removed when the cap is decoupled from the housing. The cap may at least temporarily maintain the needle guard in the extended position. Movement of the plunger may expel medicament from the medicament chamber through the needle. The needle guard may be moveable to a lockout position and the needle guard may include a needle guard lock that engages a lockout surface to prevent proximal movement of the needle guard when the needle guard is in the lockout position. The needle guard lock may include a lockout arm that flexes radially outwardly to engage the lockout surface when the needle guard is in the lockout position. In a further embodiment, a collar is coupled to the housing, the collar including the lockout surface. In a further embodiments, a biasing element is coupled to the collar and the needle guard, the biasing element biasing the needle guard toward the extended position.

BRIEF DESCRIPTION OF THE SEVERAL VIEWS OF THE DRAWINGS

The following detailed description of embodiments of the auto-insert injector, will be better understood when read in conjunction with the appended drawings of an exemplary embodiment. It should be understood, however, that the invention is not limited to the precise arrangements and instrumentalities shown. For example, although not expressly stated herein, features of one or more various disclosed embodiments may be incorporated into other of the disclosed embodiments.

In the drawings.

DETAILED DESCRIPTION OF THE EXEMPLARY EMBODIMENTS OF THE INVENTION

Figure 1:
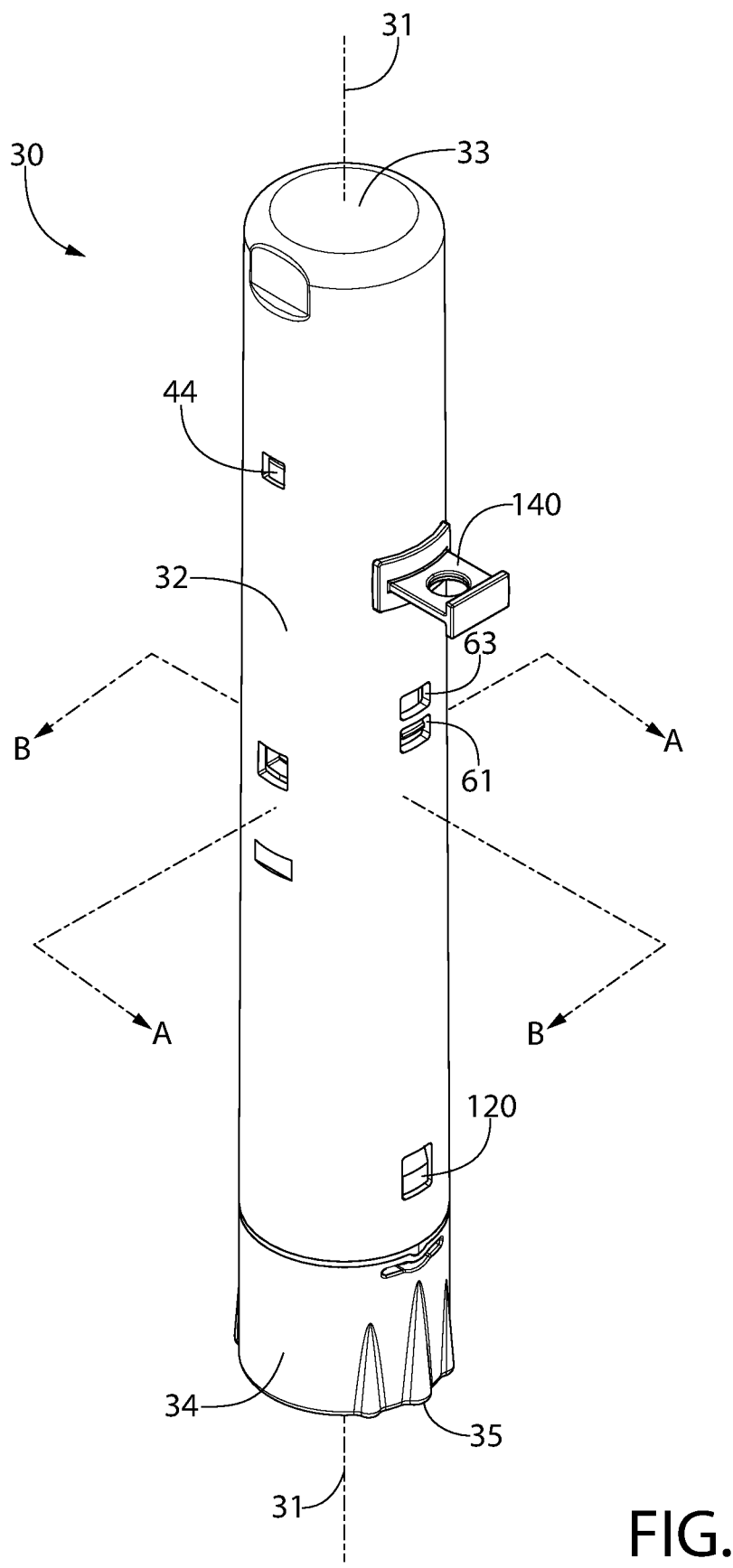
FIG. 1 is a perspective view of an injector in accordance with an exemplary embodiment of the present invention.
Figure 2:
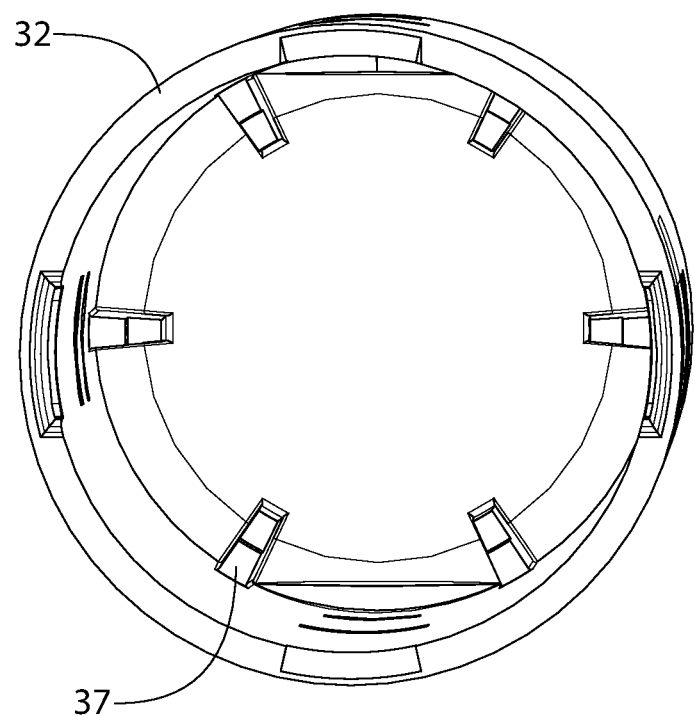
FIG. 2 is a bottom elevational view of the housing of FIG. 1.

Referring to the drawings in detail, wherein like reference numerals indicate like elements throughout, there is shown in FIGS. 1-27 an injector, generally designated 30, in accordance with an exemplary embodiment of the present invention. In some embodiments, the injector 30 is configured to auto-insert a needle into a patient or user in response to an activation.

The injector 30 may be configured to inject medicament into a user or patient. The injector 30 may be configured to receive a syringe or the injector may include a medicament chamber. The medicament may be for example, but not limited to, diazepam, haloperidol, lorazepam, methotrexate, testosterone, or recombinant human papillomavirus quadrivalent. The injector 30 may be configured to deliver medicament subcutaneously or intramuscularly. The injector 30 may be configured to insert a needle to a selected insertion depth. The injector 30 may include a retractable needle guard and the insertion depth may be independent of the length of travel of the retractable needle guard. The injector 30 may include an inner assembly insertable into an outer housing and the inner assembly may be assembled before coupling the outer housing to the inner assembly. The injector 30 may move a needle relative to a housing to an insertion depth before delivering medicament through the needle. The injector 30 may include a needle shield remover configured to engage a portion of a rear surface of a needle shield. The needle shield remover may be part of the inner assembly. The inner assembly may allow visual confirmation that the needle shield remover is engaged with a rear surface of the needle shield before completing assembly of the injector 30.

Figure 3:
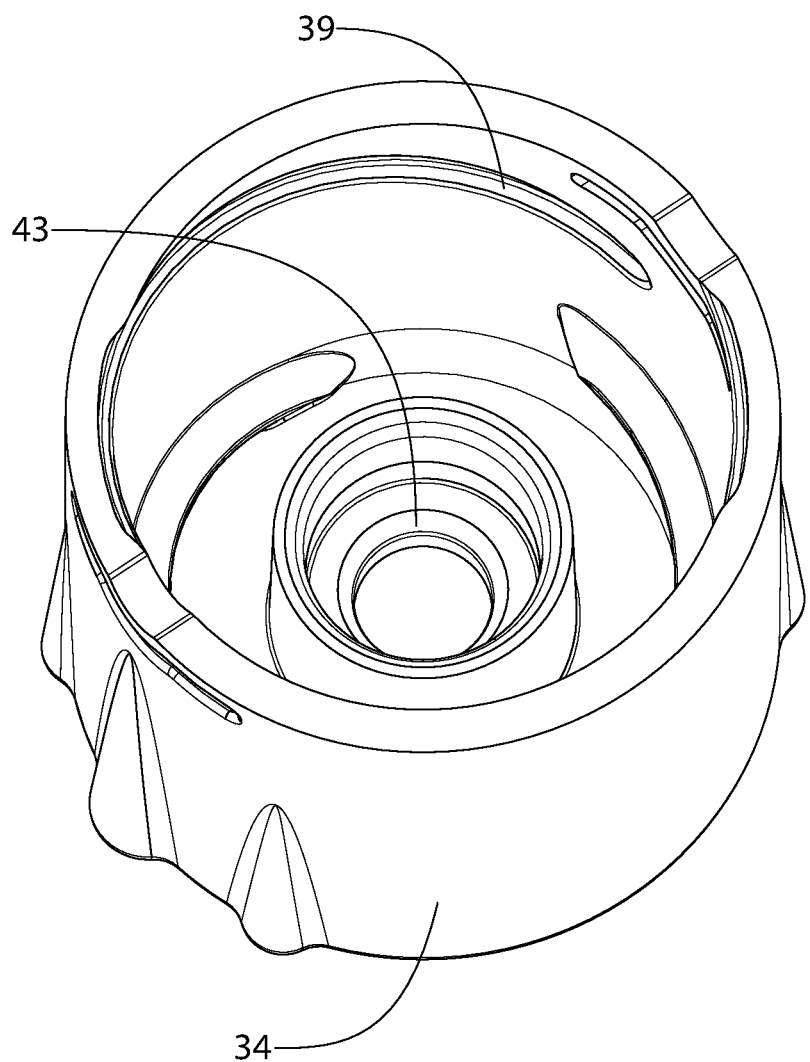
FIG. 3 is a top perspective view of the cap of FIG. 1.
Figure 4:
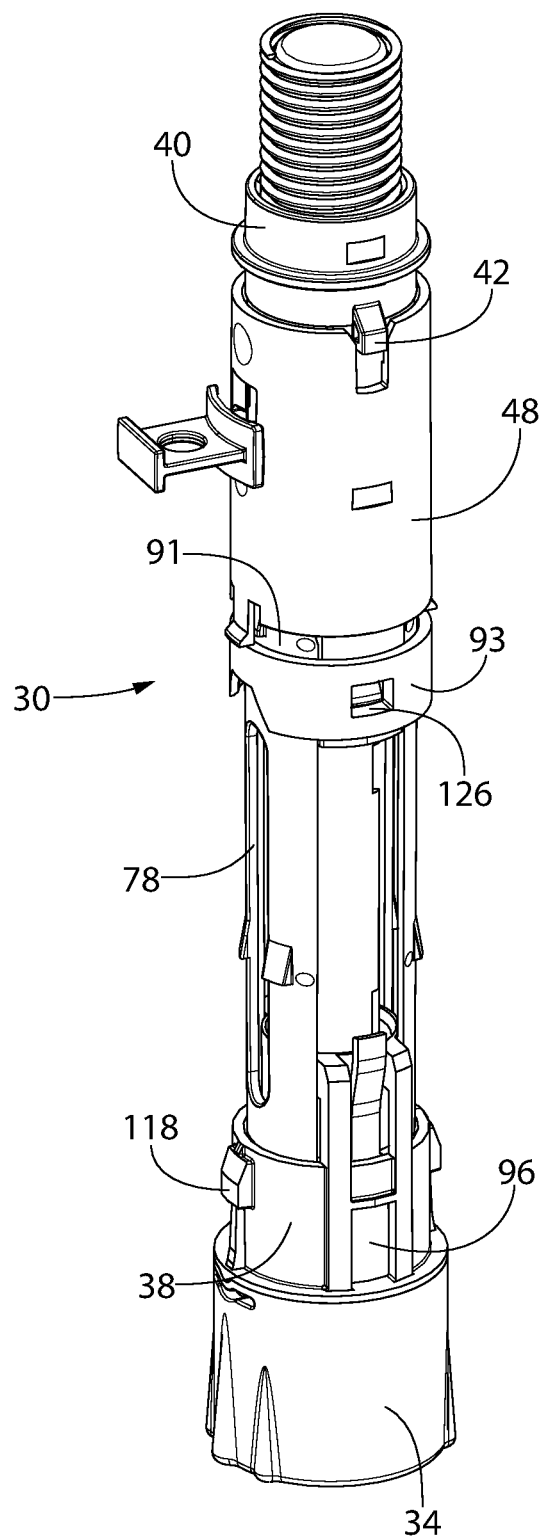
FIG. 4 is a perspective view of the injector of FIG. 1 with the housing removed.
Figure 5:
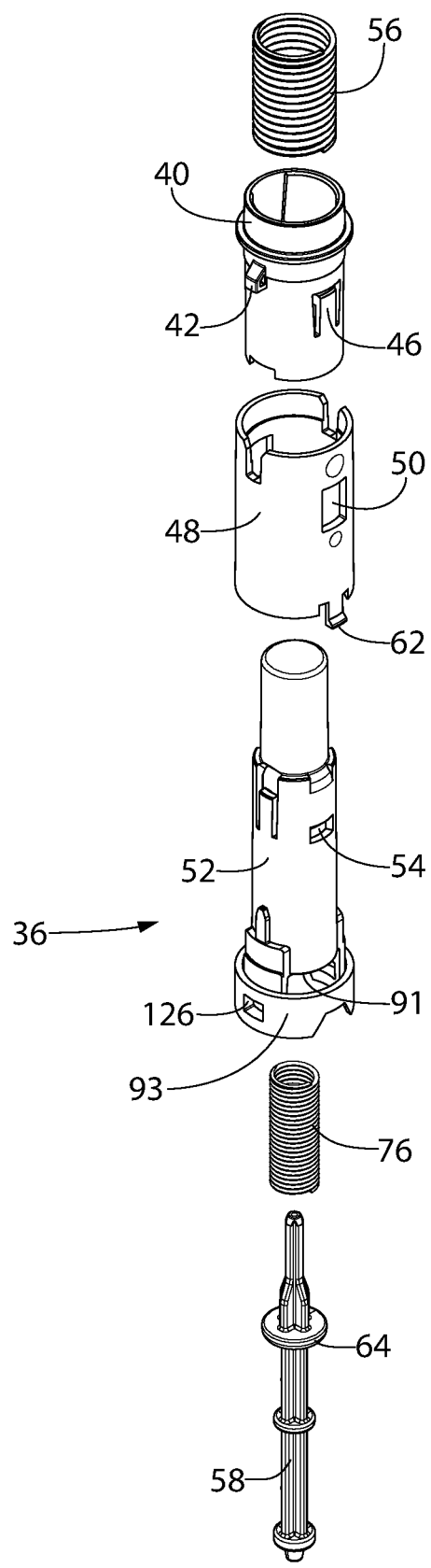
FIG. 5 is an exploded view of an inner assembly of the injector of FIG. 1.

Referring to FIGS. 1-5, the injector 30 may include a housing 32. The housing 32 include a cavity to at least partially receive an inner assembly 36 (FIGS. 4-5). The inner assembly 36 may be configured to move a needle relative to the housing 32 and discharge medicament from a reservoir out of the needle. One or more alignment features 37 (e.g., protrusion or ridge) may be within the internal cavity of the housing 32. The alignment feature 37 may align the inner assembly 36 relative to the housing 32. In some embodiments, the housing 32 has a cylindrical outer shape. In other embodiments, the housing 32 has an outer shape configured to prevent the injector 30 from rolling when placed on a surface. The injector 30 may include a longitudinal axis 31 extending from a proximal end 33 to a distal end 35 of the housing 32.

Figure 13:
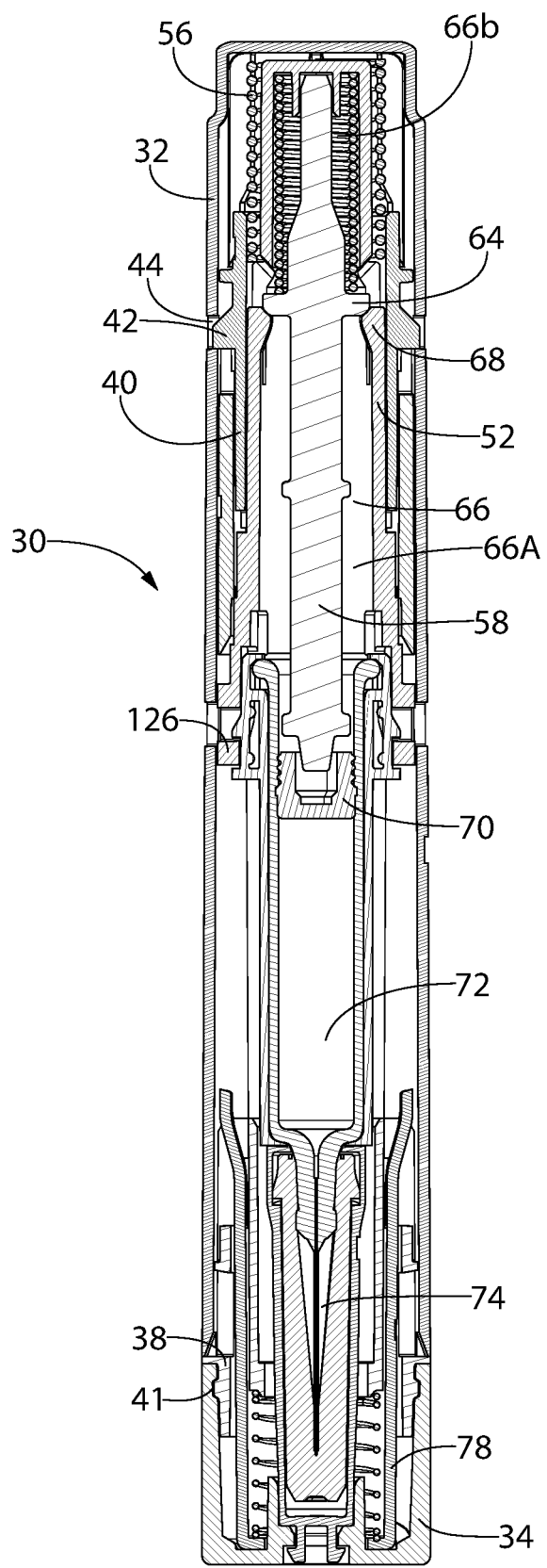
FIG. 13 is a sectional view of the injector of FIG. 1 taken along a plane including line A-A in a pre-firing configuration.
Figure 14:
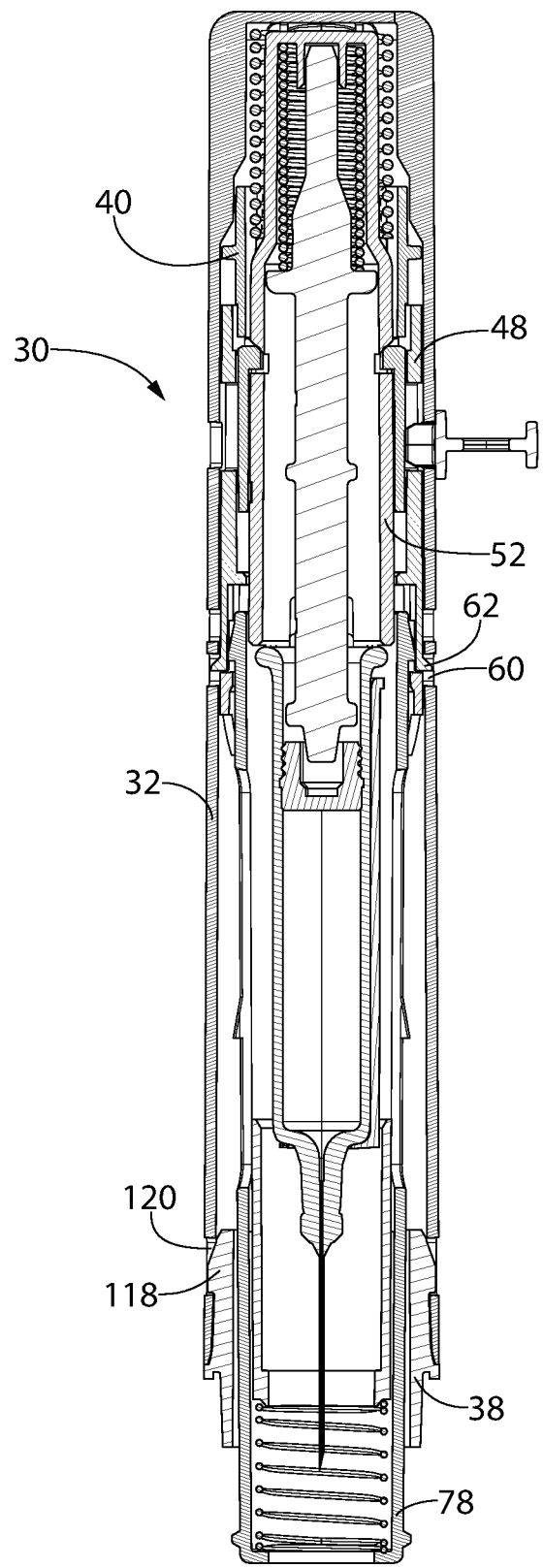
FIG. 14 is a sectional view of the injector of FIG. 1 taken along a plane including line B-B.

Referring to FIGS. 3-4 and 13, the injector 30 may include a cap 34 configured to prevent unintended retraction of a needle guard or unintended exposure of the needle (e.g., during manufacture, transportation, or prior to an intended use). The cap 34 may be detachably coupled to the housing 32 or a collar 38 (FIG. 13). The cap 34 may be decoupled from the housing 32 or collar 38 (e.g., by pulling, pushing, or twisting the cap 34 relative to the housing 32 or collar 38). At least one of the cap 34 and the collar 38 may include a recess or thread 39 to receive a protrusion or mating thread 41 on the other of the cap 34 and the collar 38. The cap 34 may be shaped and dimensioned to prevent the injector 30 from rolling when the cap is attached to the injector and the injector is placed on a surface. The collar 38 may include a collar protrusion 118 (FIG. 4) configured to be received by a second aperture 120 on the housing 32 (e.g., via snap fit), thereby fixing the collar 38 to the housing 32 (FIG. 14). The cap 34 may include a receiver 43. The receiver 43 may be configured to couple to a needle shield remover, as explained in greater detail below.

Referring to FIGS. 5, the injector 30 may include an inner assembly 36. The inner assembly 36 may be configured to move a syringe relative to the housing 32 and to deliver medicament from the syringe to a user or patient. The inner assembly 36 may include a first member 48, a second member 40, and a shell 52. The inner assembly 36 may include a ram 58 and an actuation assembly configured to move at least one of the shell 52 and the ram 58 with respect to the housing 32. The first member 48, second member 40, shell 52, and ram 58 may nest within each other within the housing. Some parts of the inner assembly 36 may be fixed to the housing 32 while other parts are moveable relative to the housing 32. The second member 40 may be fixed relative to the housing 32 and the first member 48 may be moveable relative to the second member 40 and the housing 32.

Referring to FIGS. 1, 4, and 13, in some embodiments, the second member 40 is fixed to the housing 32 by a protrusion 42 (FIG. 4) positioned in an aperture 44 (FIG. 1) of the housing 32. In other embodiments, the second member 40 includes an aperture configured to receive a protrusion on the housing 32. The protrusion 42 may be coupled to the housing 32 via a snap fit. In other embodiments, the second member 40 is fixed to the housing 32 via adhesive, welding, or fastener.

Figure 15:
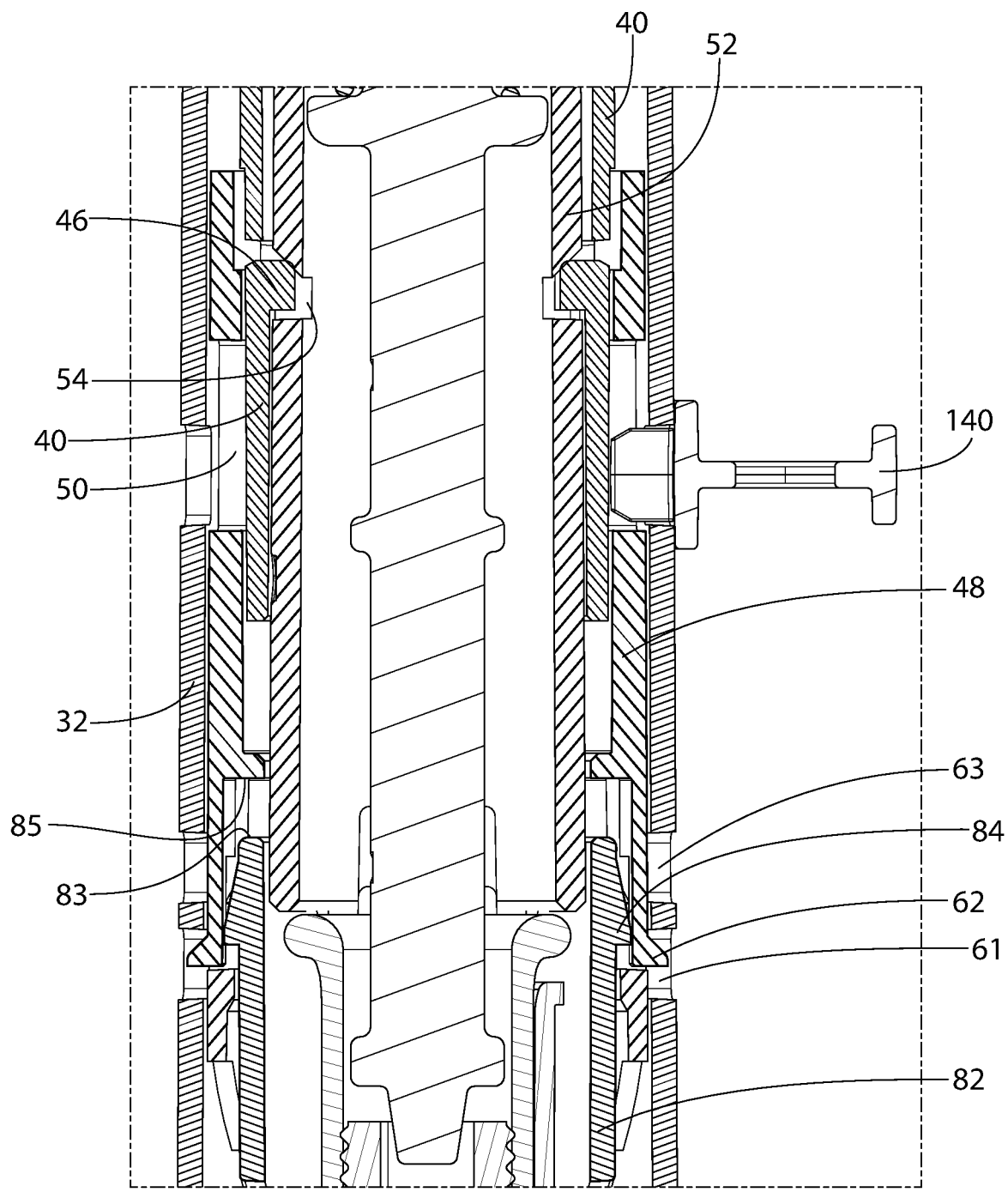
FIG. 15 is a close-up view of a portion of the sectional view of FIG. 14.
Figure 19:
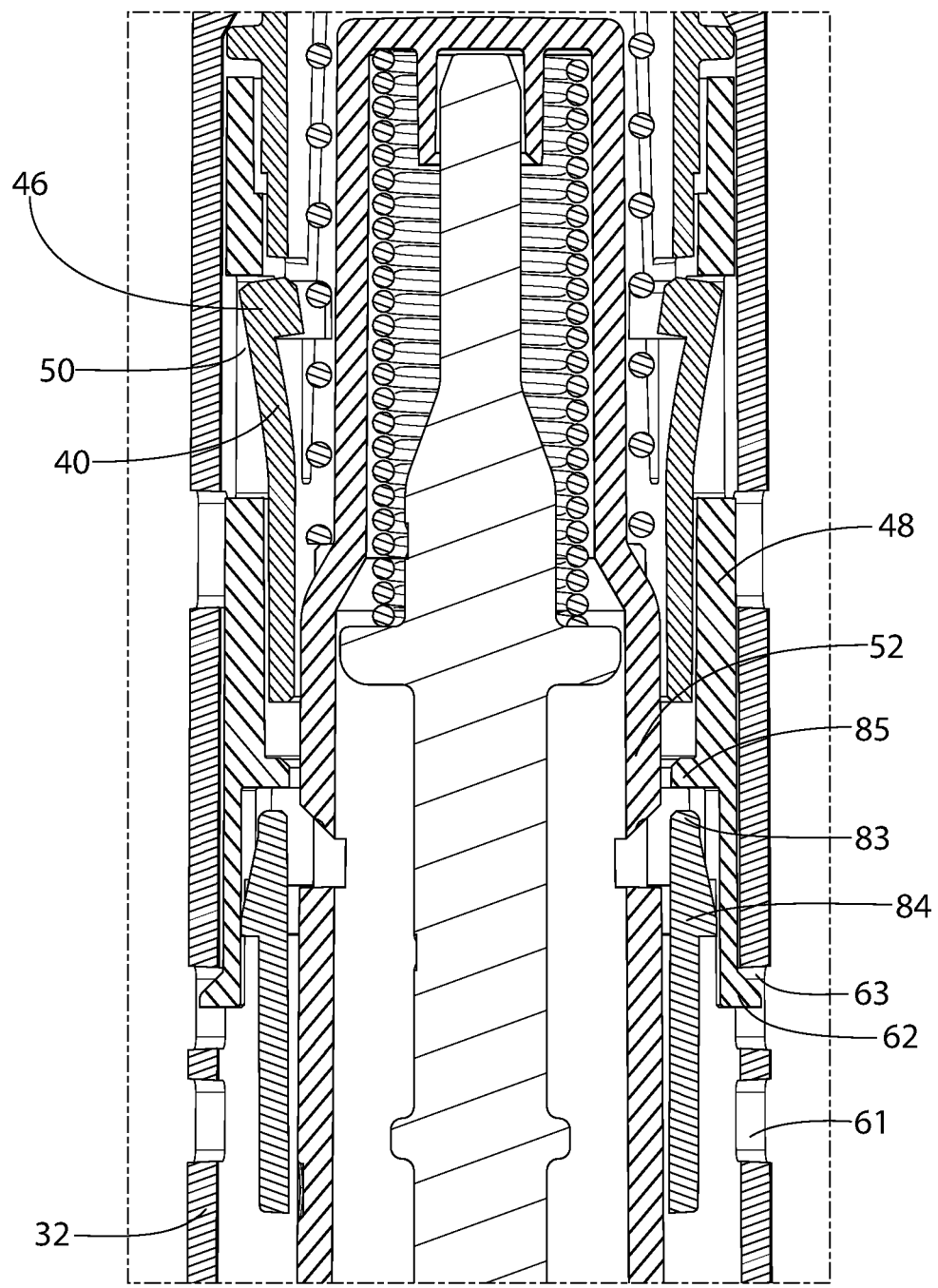
FIG. 19 is a close-up view of a portion of the sectional view of FIG. 18.

Referring to FIGS. 4, 15, and 19, the second member 40 may include a first arm 46 or catch. The first arm 46 may engage and prevent movement of the shell 52 relative to the housing 32. The first arm 46 may be configured to move from a first position (FIG. 15) to a second position (FIG. 19). The first arm 46 may deflect radially outwardly as the arm moves from the first position to the second position. In some embodiments, the first arm 46 is biased toward the second position but a first member 48 blocks movement of the first arm 46 until the injector 30 is activated. In other embodiments, the first arm 46 is at rest in the first position but movement of the shell 52 relative to the housing 32 forces the first arm 46 from the first position to the second position.

Referring to FIGS. 4-5, the first member 48 may be configured to at least partially receive the second member 40. The first arm 46 of the second member 40 may be in the first position when the second member 40 is received by the first member 48. The first member 48 may at least partially surround the second member 40 such that the first member 48 blocks movement of the first arm 46. The first member 48 may be moveable (e.g., axially translatable, rotatable) relative to the housing 32 or second member 40. The first member 48 may include a recess or opening 50. The first arm 46 may move from the first position to the second position when the first arm 46 is aligned with the opening 50. The opening 50 may be aligned with the first arm 46 when the first member 48 is moved relative to the second member 40. The second member 40 may remain fixed relative to the housing 32 as the first member 48 moves relative to the second member 40.

Referring to FIGS. 1 and 15, a safety 140 may be positioned in the opening 50 when the injector 30 is in a safe state. The safety 140 may extend through an opening in the housing 32. The safety 140 may engage a sidewall of the opening in the housing 32 such that the safety 140 is prevented from moving axially along the axis 31. The safety 140 may be detachably coupled to the housing 32. The safety 140 may prevent axial movement of the first member 48. The safety 140 may be manually removed from the housing 32 such that the injector 30 may be activated as described herein. In some embodiments, the safety 140 is coupled to the housing 32 during manufacturing and is removed once the injector 30 is assembled. The safety 140 may be removed prior to the injector 30 being provided to a user. In other embodiments, the safety 140 is removed by a user prior to using the injector 30.

Referring to FIGS. 1, and 4-5, the first member 48 may include a detent 62. The detent 62 may be moveable relative to the first member 48 from a first position (e.g., relaxed position) to a second position (e.g., a radially flexed position). The detent 62 may include a cantilevered arm extending from the first member 48. The detent 62 may be configured to engage a sidewall of a first detent opening 61 or second detent opening 63 in the housing 32 (FIG. 1) as explained in greater detail below.

Figure 18:
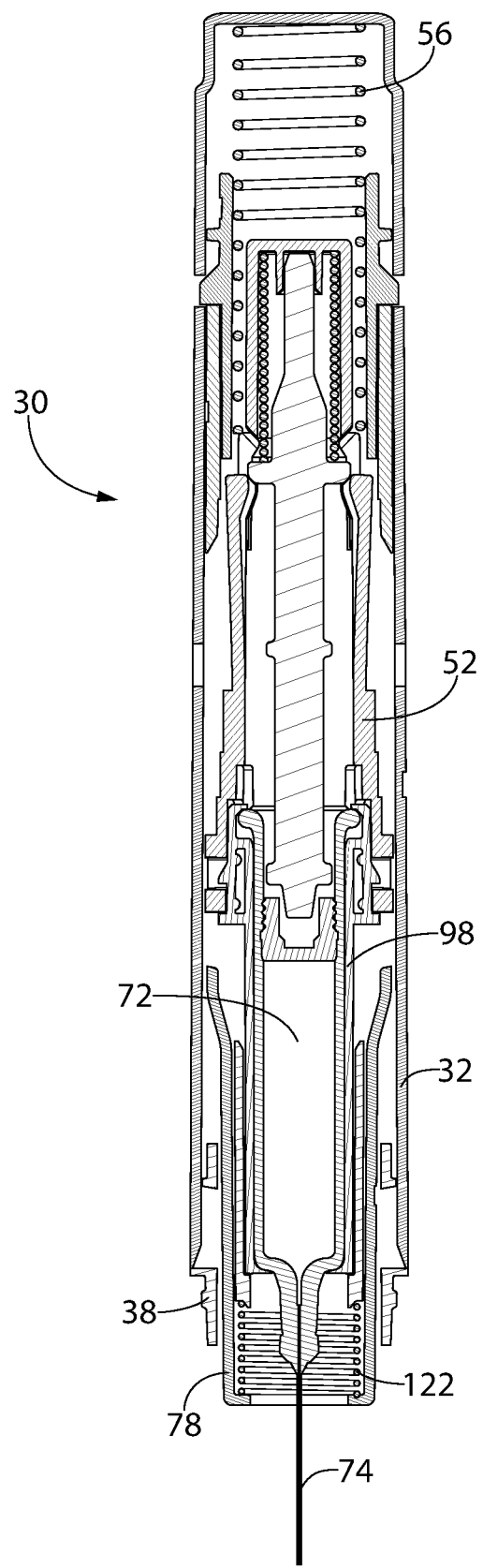
FIG. 18 is a sectional view of the injector of FIG. 1 in an injecting configuration.

Referring to FIGS. 4-5 and 15, the shell 52 may be configured to be coupled to a syringe carrier. The shell 52 may be moveable with respect to the housing 32 from an initial position (FIG. 13) to an injecting position (FIG. 18). The shell 52 may be positioned with the housing 32. The second member 40 may at least partially encircle the shell 52. The shell 52 may include a first recess 54 on an outer surface thereof. The first recess 54 may extend through a sidewall of the shell 52. The first recess 54 may be configured to receive a portion of the first arm 46 of the second member 40 to at least temporarily fix the shell 52 relative to the second member 40. The first arm 46 may be positioned within the recess 54 when the first arm 46 is in the first position.

Still referring to FIGS. 4-5 and 15, the shell 52 may be moveable (e.g., axially translatable, rotatable) relative to the housing 32 or second member 40. The first arm 46 may engage a sidewall of the first recess 54 to prevent the shell 52 from moving relative to the housing 32. At least one the recess 54 and the first arm 46 may have a chamfered edge such that axial movement of the shell 52 causes radial movement of the first arm 46.

Still referring to FIGS. 4-5 and 13, the shell 52 may include an inner recess 66 or cavity configured to at least partially receive a ram 58 (FIG. 13). In some embodiments, the inner recess 66 is configured to receive a syringe 72. In other embodiments, the inner recess 66 defines a medicament chamber. The shell 52 may include an engagement member 68 configured to at least temporarily hold the ram 58 in a pre-firing position. The shell 52 may include a plurality of engagement members 68 spaced circumferentially about the perimeter of the shell 52. The engagement member 68 may include a flexible arm that at least temporarily blocks movement of the ram 58. The engagement member 68 may be biased radially outwardly. The engagement member 68 may be moveable between an engaged position (FIG. 13) wherein the engagement member 68 prevents movement of the ram 58 and a disengaged position (FIG. 22) wherein the ram 58 can move with respect to the shell 52. The second member 40 may prevent movement of the engagement member 68 between the engaged position and the disengaged position. The engagement member 68 may be in the engaged position when the shell 52 is in the initial position. The engagement member 68 may be in the disengaged position when the shell 52 is in the injecting position.

Referring to FIGS. 4-5 and 13, the ram 58 may include a rim 64 configured to engage the engagement member 68 when the injector 30 is in the pre-firing configuration (FIG. 13). The ram 58 may be configured to engage a plunger 70. The plunger 70 may move relative to the shell 32 as the ram 58 moves relative to the shell 52 to force medicament out of a medicament chamber (e.g., in a prefilled syringe), through a needle 74, and into a patient or user. The rim 64 may have a larger diameter than the internal diameter of the medicament chamber such that the rim 64 cannot enter the medicament chamber. The rim 64 of the ram 58 may be spaced from the flange 106 of the syringe 72 when the plunger 70 is at the end of the medicament chamber.

Referring to FIGS. 5 and 13, the injector 30 may include an actuation assembly configured to move the shell 52 from the initial position to the injecting position. The actuation assembly may be coupled to the housing 32 and the shell 52. The actuation assembly may be operatively associated with the housing 32 and the shell 52. The actuation assembly may include a first biasing element 56. The first biasing element 56 may be operatively associated with the housing 32 and the shell 52. The first biasing element 56 may urge the shell 52 toward the distal end 35 of the injector 30.

Still referring to FIG. 13, the actuation assembly may include a second biasing element 76. The actuation assembly may include first biasing element 56 and second biasing element 76. The second biasing element 76 may be positioned within the inner recess 66 of shell 52. The second biasing element 76 may be operatively associated with the shell 52 and the ram 58. The second biasing element 76 may engage the rim 64 of the ram 58 and an end of the shell 52 such that the ram 58 is biased toward the distal end 35 of the injector 30. In some embodiments, the second biasing element 76 does not move the ram 58 until the shell 52 is in the injecting position. The actuation assembly may cause movement of the plunger 70 with respect to the shell 52 when the shell 52 is in the injecting position.

Referring to FIG. 13, the inner recess 66 of the shell 52 may include a first portion 66a and a second portion 66b. The second portion 66b may be proximal to the first portion 66a. The first portion 66a may be configured to receive a portion of the ram 58 and the rim 64. The second portion 66b may be configured to receive a proximal end of the ram 58 and a second biasing element 76. The second portion 66b may have a smaller diameter than the first portion 66a. The first portion 66a may have a greater axial length than the second portion 66b.

Figure 6:
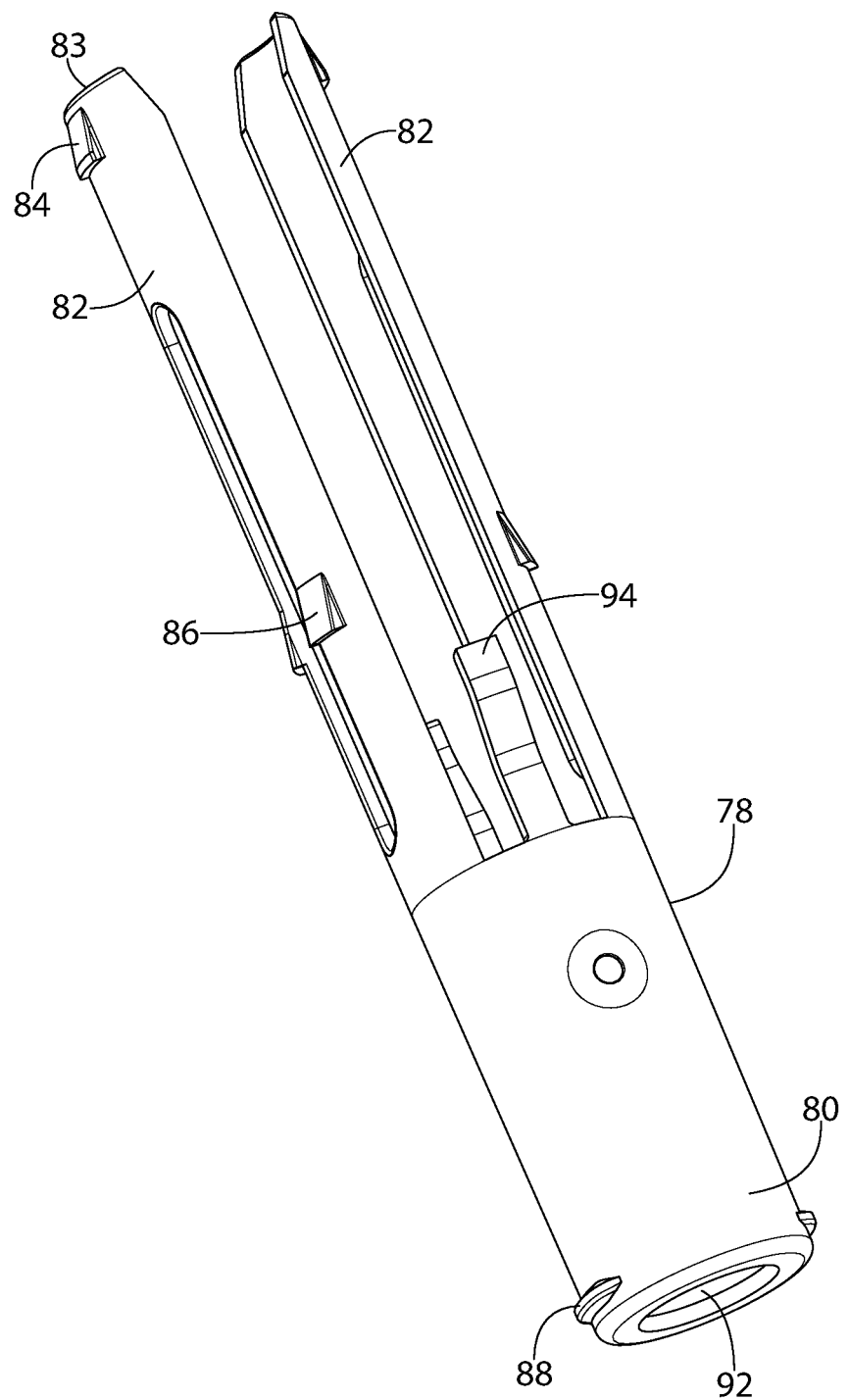
FIG. 6 is a perspective view of a needle guard of the injector of FIG. 1.
Figure 20:
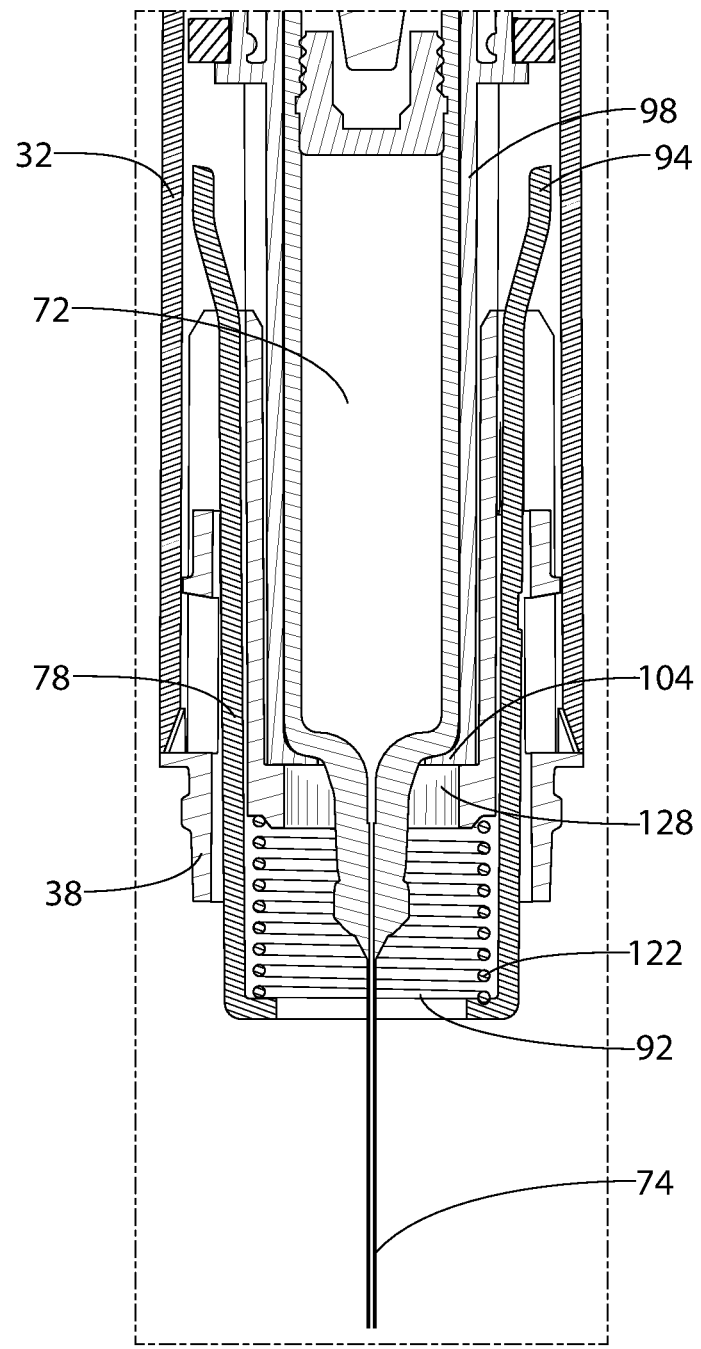
FIG. 20 is a close-up view of a portion of the sectional view of FIG. 18.

Referring to FIGS. 6, 14, and 20, the injector 30 may include a needle guard 78. The needle guard 78 may surround the needle 74 when the injector 30 is not in use. The needle guard 78 may be moveable relative to the housing 32 from an extended position (FIG. 14) to a retracted position (FIG. 20). The needle guard 78 may be configured to be moved by a user when a distal end of the needle guard 78 is positioned against an injection site (e.g., against a user's skin) and a force is applied to the distal end of the injector 30 such that the needle guard 78 moves proximally relative to the housing 32. The needle guard 78 may include a base 80 (FIG. 6). At least a portion of the base 80 may extend from the housing 32 when the injector 30 is in the pre-firing configuration. The needle guard 78 may include a leg 82 extending from the base 80. The leg 82 may include a needle guard protrusion 84 configured to engage the detent 62 of the first member 48, as explained in greater detail below. The leg 82 may include an engagement surface 83 configured to engage the first member 48. The engagement surface 83 may be at a proximal end of the leg 82. The leg 82 of the needle guard 78 may extend through an opening 91 in a rim 93 (FIG. 4) of the shell 52. The rim 93 may maintain alignment of the leg 82. The rim 93 may prevent undesired flexing of the leg 82 of the needle guard 78.

Referring to FIG. 6, the needle guard 78 may include a limiter 86 configured engage a protrusion or recess on the housing 32 or collar 38 to limit distal movement of the needle guard 78 relative to the housing 32 after the injector 30 has been fired. The needle guard 78 may include a cap engagement feature 88 (FIG. 6) configured to engage a feature (e.g., a thread or another protrusion) on the cap 34 to prevent unintended movement of the needle guard 78. The needle guard 78 may be axially fixed relative to the housing 32 when the cap 34 is coupled to the housing 32 and needle guard 78. The needle guard 78 may include an opening 92 configured to allow the needle 74 to pass therethrough when the injector 30 is fired. The needle guard 78 may include a lockout arm 94 (FIG. 6) configured to be positioned in a lockout opening 96 in the collar 38 (FIG. 25) after the injector 30 has been fired, as explained in greater detail below.

Figure 7:
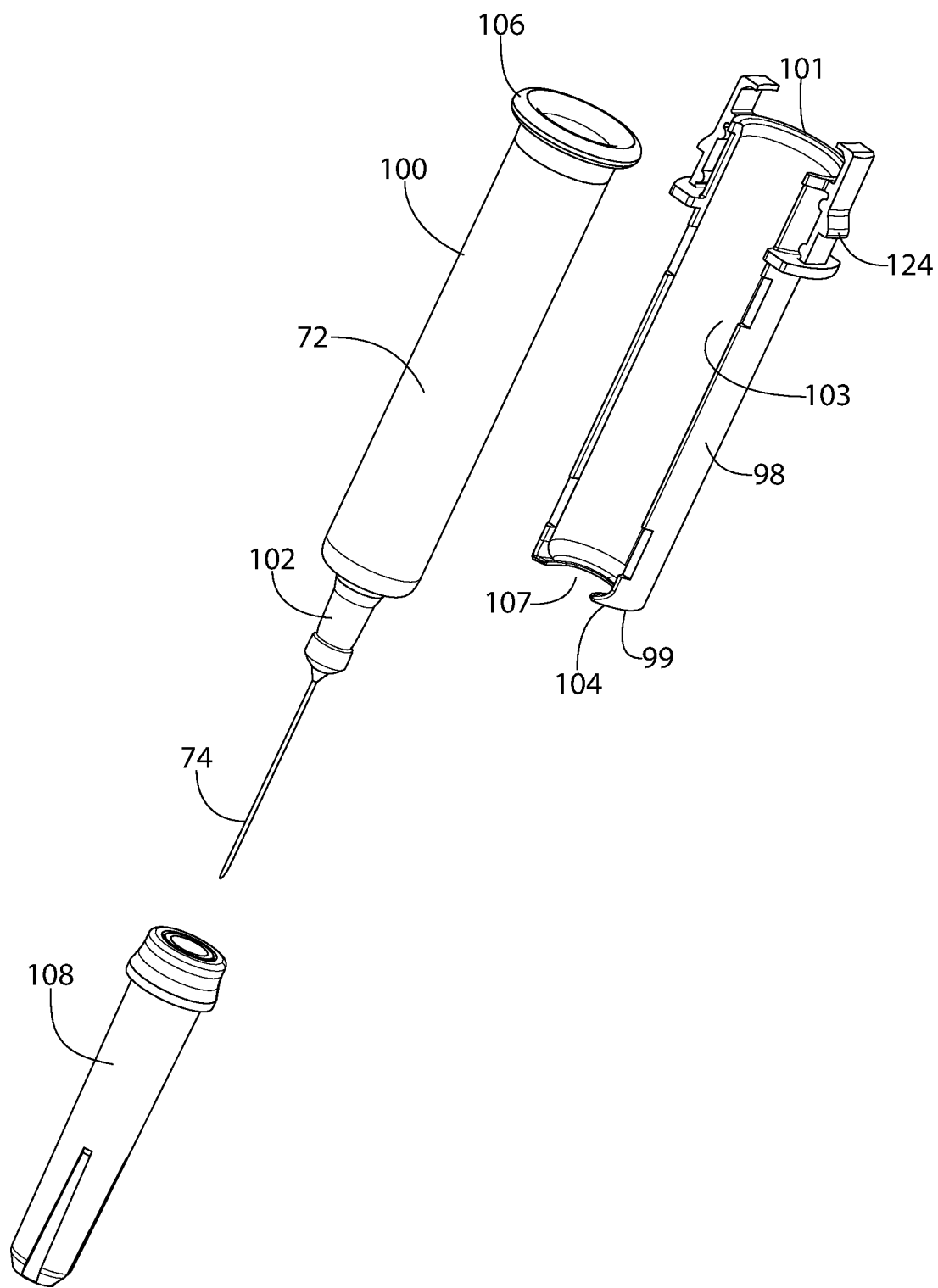
FIG. 7 is a perspective exploded view of a syringe assembly of the injector of FIG. 1.

Referring to FIG. 7, the injector 30 may include a syringe 72 (e.g., a pre-filled syringe). The syringe 72 may include a body 100 defining a medicament chamber and a neck 102 adjacent the body 100. The body 100 may have a first diameter and the neck 102 may have a second diameter. The first diameter may be larger than the second diameter. The needle 74 may be coupled to the neck 102. The needle 74 may be in fluid communication with the medicament chamber. The plunger 70 may be positioned within the medicament chamber. The plunger 70 may move relative to the medicament chamber to eject medicament from the medicament chamber out through the needle 74. The syringe 72 may include a syringe flange 106. The syringe flange 106 may have a larger diameter than the body 100.

Referring to FIGS. 7-11, the syringe 72 may be positioned in a syringe holder 98. The syringe holder 98 may include a c-shape or a partial cylinder shape such that the syringe 72 can be loaded from a side of the syringe holder 98. The syringe holder 98 may include a first end 99 and a second end 101. A sidewall 103 may extend from the first end 99 to the second end 101. The sidewall 103 may define a receiving area for the syringe 72. The sidewall 103 may include an opening extending from the first end 99 toward the second end 101. The sidewall opening may extend from the first end 99 to the second end 101. The syringe 72 may be moved through the sidewall opening such that the syringe 72 may be loaded into the syringe holder 98 from a side of the syringe holder 98. The syringe 72 may be loaded into the syringe holder 98 without moving the syringe 72 axially through a rear opening of the syringe holder 98. The syringe 72 may be loaded into the syringe holder 98 without passing the needle shield 108 through the syringe holder 98. In some embodiments, the syringe 72 is snap fit into the syringe holder 98. In some embodiments, the sidewall 103 is flexible such that the sidewall 103 resiliently deforms as the syringe 72 moves through the sidewall opening.

Figure 8:
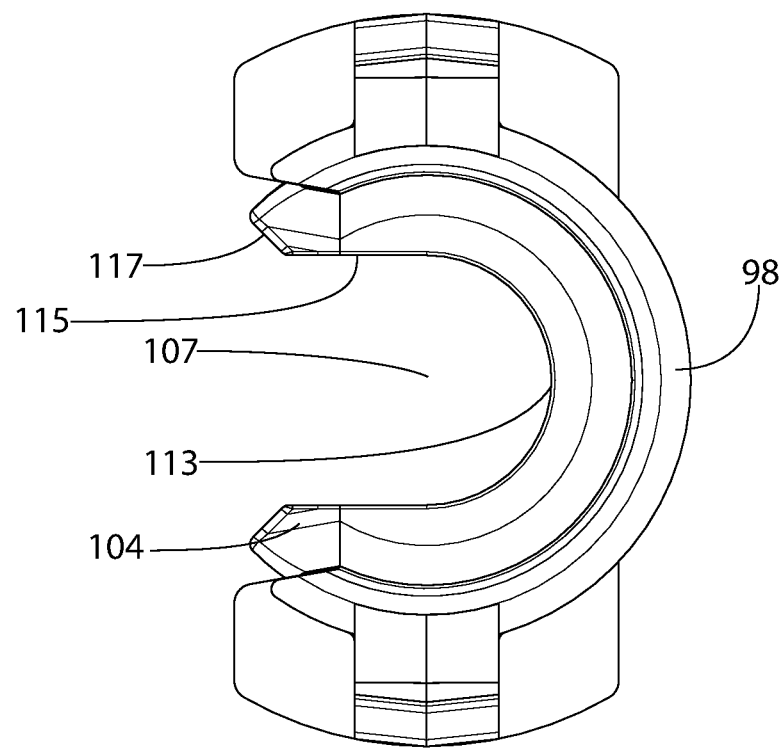
FIG. 8 is a top plan view of the syringe carrier of FIG. 1.
Figure 9:
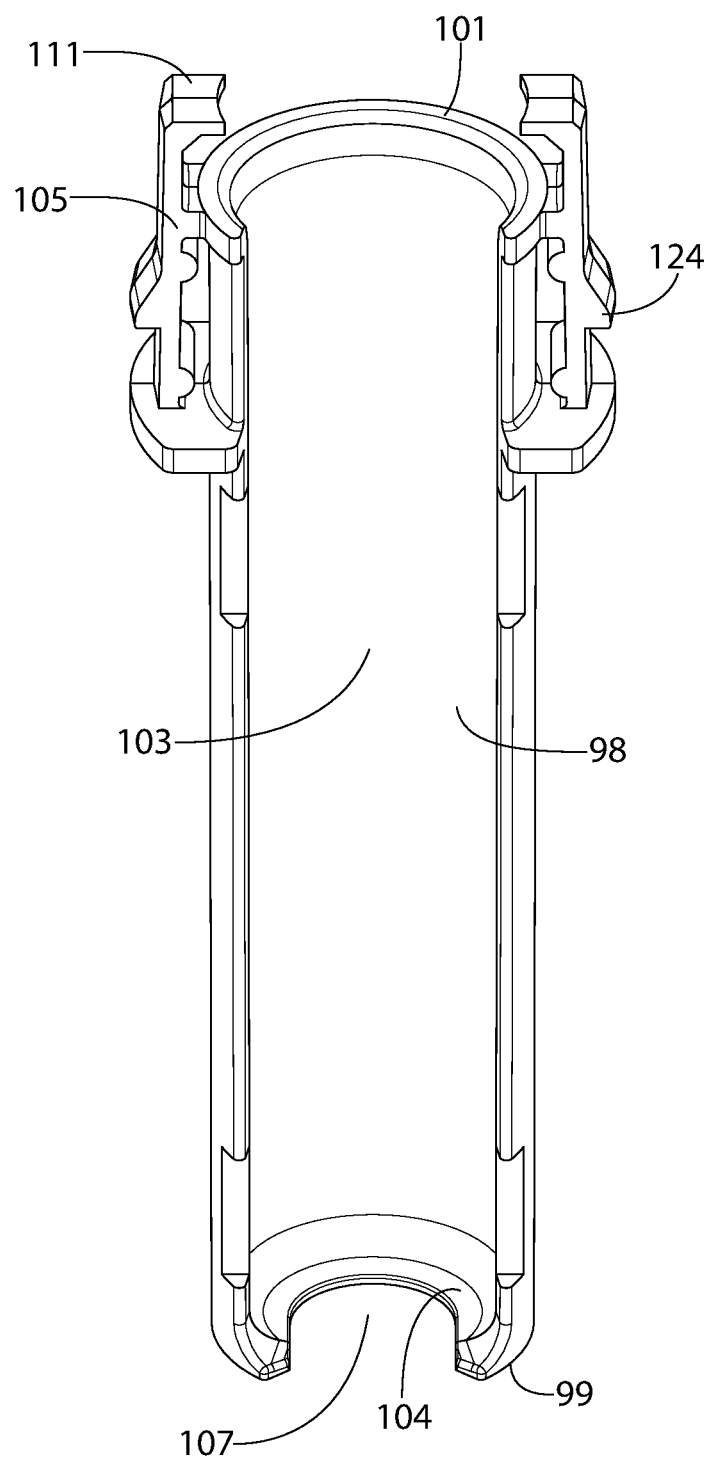
FIG. 9 is a perspective view of the syringe carrier of FIG. 1.

Still referring to FIGS. 7-9, the syringe holder 98 may include an end wall 104 configured to engage an end of the body 100 of the syringe 72 adjacent the neck 102. The end wall 104 may extend radially inward from the sidewall 103 of the syringe holder 98. The end wall 104 may limit or prevent movement of the syringe 72 relative to the syringe holder 98 when the injector 30 is fired. The end wall 104 may include an end wall opening 107 configured to receive the neck 102 of the syringe 72. The size of the end wall opening 107 may be selected such that a portion of the end wall 104 contacts the lower portion of the syringe 71. The end wall opening 107 may include an opening circumscribing an arc of at least 180 degrees. The end wall opening 107 may include an arcuate portion 113 (FIG. 8) having a radius of about 0.1 inches, about 0.15 inches, about 0.2 inches, about 0.3 inches, about 0.4 inches, or about 0.5 inches. The end wall opening 107 may include a straight portion 115 that is tangent to the arcuate portion 113. The neck 102 of the syringe 72 may be engaged by the arcuate portion 113 and the straight portion 115 when the syringe 72 is within the syringe holder 98. The end wall opening 107 may include a chamfered edge 117. The chamfered edge 117 may provide a lead in to make it easier for a user or manufacturer to load the neck of the syringe 72 into the end wall opening 107. The end wall 104 may be rigid.

Still referring to FIGS. 7-9, the syringe holder 98 may include syringe holder arms 105. The syringe holder arms 105 may include a lip 111 configured to retain the syringe 72. The syringe flange 106 may be positioned between the lip 111 and the second end 101 of the syringe holder 98. The syringe flange 106 may be spaced from the second end 101 of the syringe holder 98 when the syringe 72 is coupled to the syringe holder 98. Spacing the syringe flange 106 from the second end 101 of the syringe holder 98 may reduce or eliminate any impact of the syringe flange 106 on the syringe holder 98 to reduce or eliminate breaking the syringe 72. The syringe holder 98 may retain the syringe 72 even if the syringe 72 breaks. The syringe holder 98 may include a fastener 124 configured to engage a ridge 126 (FIGS. 4 and 13) on the shell 52 to fix the syringe holder 98 relative to the shell 52. The fastener 124 may be snap fit into the ridge 126. The arms 105 may include the fastener 124 to engage the ridge 126 on the shell 52 and the lip 111 to engage the syringe flange 106.

Referring to FIGS. 7-11, a needle shield 108 may cover the needle 74 when the injector 30 is in the pre-fired configuration. The needle shield 108 may have an outer diameter greater than the diameter of the end wall opening 107 on syringe holder 98 (FIGS. 8-9). The needle shield 108 may have an outer diameter that is equal to or greater than the diameter of the syringe body 100. The end wall opening 107 may have a diameter that is smaller than an outer diameter of body 100. The diameter of the end wall opening 107 may be smaller than an outer diameter of the needle shield 108.

Existing syringe holders may include a tube shape wherein the syringe and needle shield are moved axially through an opening in one end of the syringe holder. The needle shields used with existing end loaded syringe holders must be smaller in diameter than the syringe because the needle shield must pass through the opening of the syringe holder.

In contrast, the syringe holder 98 can be used with a needle shield 108 having a larger diameter than syringe 72 because the needle shield 108 does not pass through the syringe holder 98 or end wall opening 107 as the syringe 72 is loaded from the side and into the syringe holder 98. The syringe 72 may be snap fit into the syringe holder 98.

Figure 10:
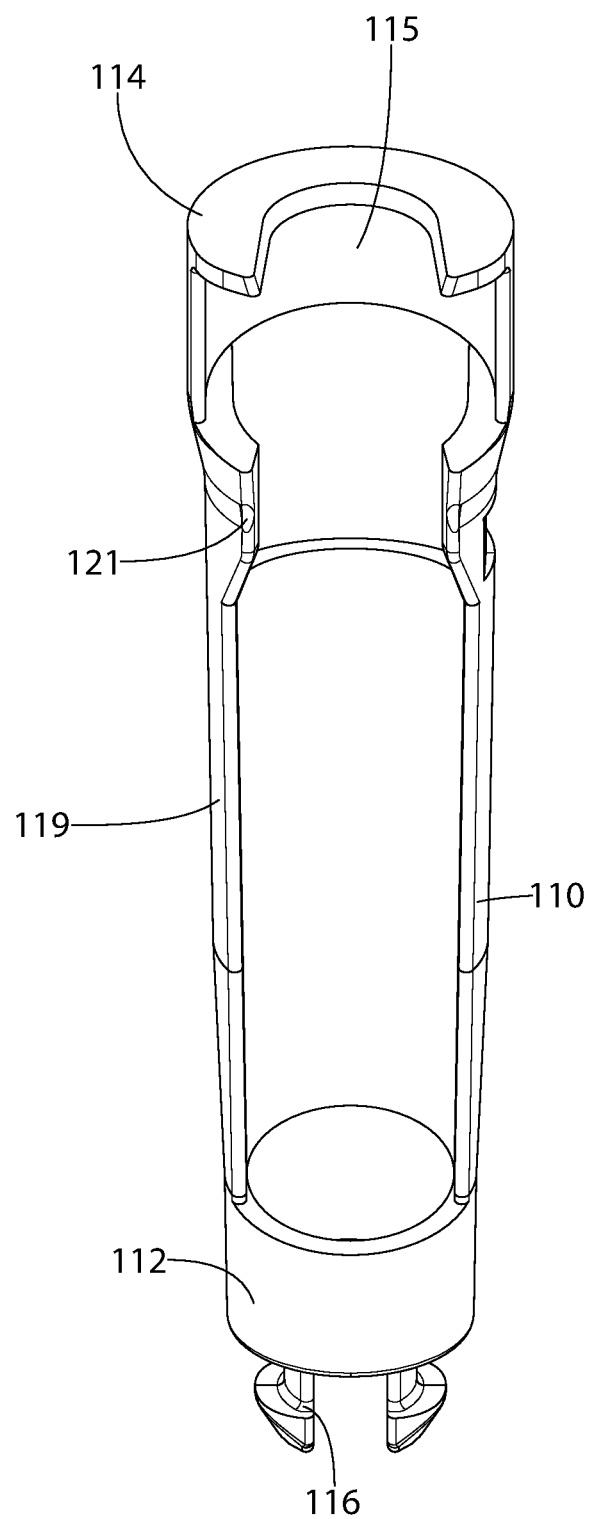
FIG. 10 is a perspective view of the needle shield remover of FIG. 1.
Figure 11:
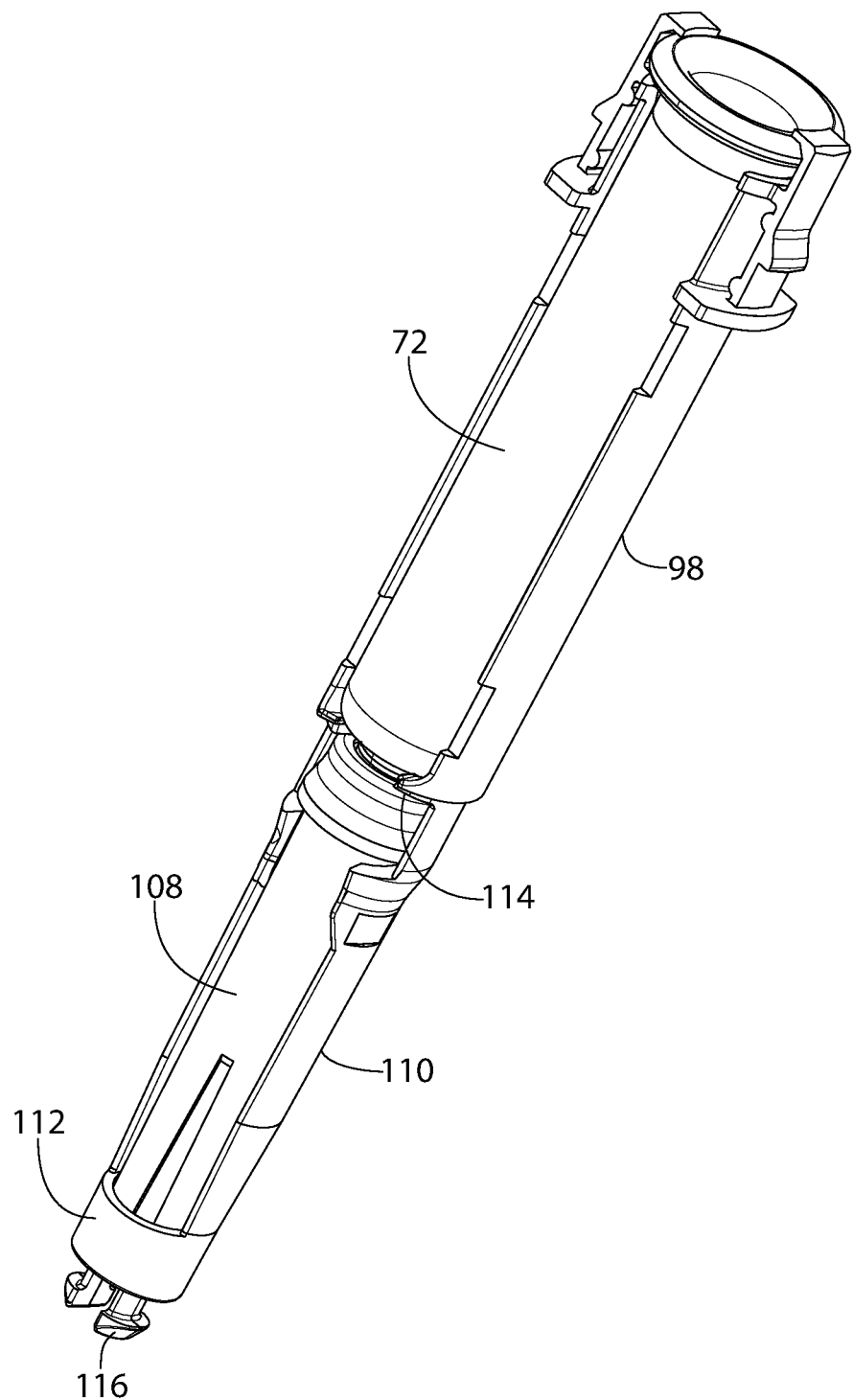
FIG. 11 is a perspective view of a syringe assembly and needle shield remover of the injector of FIG. 1.

Referring to FIGS. 10-11, the injector 30 may include a needle shield remover 110. The needle shield remover 110 may have a c-shape or a partial cylinder shape such that the needle shield 108 can be loaded from the side of the needle shield remover 110. The needle shield 108 may be snap fit into the needle shield remover 110. The needle shield remover 110 may include a sidewall 119 defining a receiving area for the needle shield 108. The sidewall may include a sidewall opening such that the needle shield can be loaded from a side through the sidewall opening. The sidewall 119 may include a neck 121. The neck 121 may snap fit over the needle shield 108 when the needle shield 108 is loaded into the needle shield remover 110. The syringe 72 and the needle shield 108 may be simultaneously loaded into the syringe holder 98 and the needle shield remover 110. The syringe 72 and the needle shield 108 may be simultaneously side loaded into the syringe holder 98 and the needle shield remover 110.

Still referring to FIGS. 10-11, the needle shield remover 110 may include a circumferential collar 112 at a distal end thereof. An end of the needle shield 108 may be loaded into the circumferential collar 112 and there may some relative rotation between the needle shield 108 and the needle shield remover 110 as the needle shield 108 is loaded into the needle shield remover 110. In some embodiments, the distal end of the needle shield 108 is loaded into the needle shield remover 110 before the proximal end of the needle shield 108 is loaded into the needle shield remover 110. The thickness of the sidewall 119 or other features of the needle shield remover 110 may be selected such that the needle shield remover 110 can receive different size needle shields 108 without changing the outer dimensions of the needle shield remover 110.

Still referring to FIGS. 10-11, the needle shield remover 110 may include a remover arm 114. The remover arm 114 may be configured to engage a proximal end of the needle shield 108. The remover arm 114 may include a projection opening 115 having a diameter that is smaller than a diameter of at least one of the needle shield 108 and the syringe 72. The remover arm 114 may be configured to engage about 10%, about 20%, about 30%, about 40%, about 50%, about 60%, about 70%, or about 80% of the surface area of the proximal end of the needle shield 108. The remover arm 114 and the end wall 104 may be positioned between an end (e.g., a proximal end) of the needle shield 108 and the end (e.g., a distal end) of the syringe 72 adjacent the neck 102 (FIG. 11).

Figure 12:
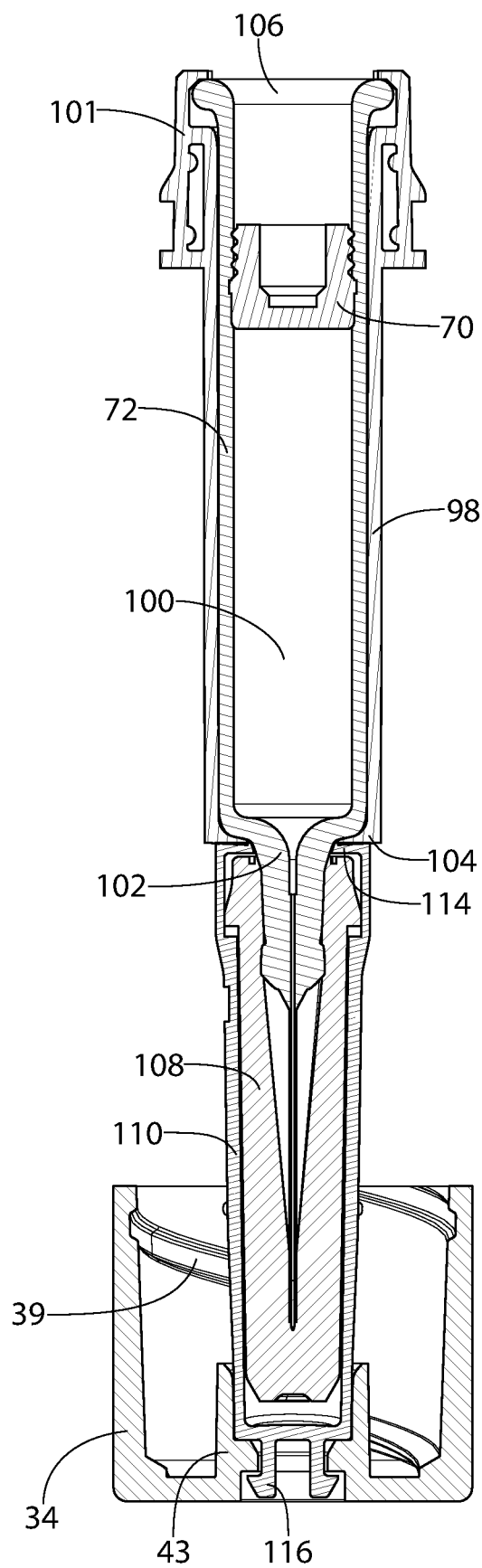
FIG. 12 is a sectional view of the syringe assembly, needle shield remover, and cap of the injector of FIG. 1 taken along a plane including line A-A.

Referring to FIGS. 3 and 11-12, the needle shield remover 110 may include a remover arm 116 configured to engage the cap 34. The remover arm 116 may be configured to be snap fit into the receiver 43 on the cap 34 (FIGS. 1 and 12). The remover arm 116 may be a flexible cantilevered beam having a protrusion on an end thereof. The protrusion may be configured to engage a ledge on the receiver 43 of the cap 34 such that the needle shield remover 110 is fixed relative to the cap 34. In some embodiments, the needle shield 108 may be coupled to the needle shield remover 110 before the needle shield remover 110 is coupled to the cap 34. In other embodiments, the needle shield 108 is coupled to the cap 34 before the needle shield 108 is coupled to the needle shield remover 110. In some embodiments, the needle shield 108 is coupled to the needle shield remover 110 before the syringe 72 is coupled to the syringe holder 98.

Referring to FIGS. 13-15, in some embodiments, the injector 30 is provided to a user in a pre-firing condition. In other embodiments, the injector 30 is provided in a safe configuration and a user may move the injector 30 to the pre-firing configuration by removing the safety 140. The cap 34 may be removed by pulling or twisting the cap 34 relative to the housing 32 such that the cap 34 is decoupled from the housing 32. The needle shield 108 may decoupled from the needle 74 and the syringe 72 when the cap 34 is removed because the needle shield remover 110 is coupled to the cap 34. The needle guard 78 may be moveable relative to the housing 32 when the cap 34 is removed from the housing 32.

Referring to FIGS. 13-15, the needle guard protrusion 84 on the leg 82 of the needle guard 78 may be positioned adjacent the detent 62 of the first member 48 when the injector 30 is in the pre-firing configuration and the needle guard 78 is in the extended position (FIG. 15). The detent 62 may be in the first position when the injector is in the pre-firing configuration. The needle guard protrusion 84 may prevent radial movement of the detent 62 from the first detent position to the second detent position when the needle guard 78 is in the extended position. The detent 62 may engage the housing 32 (e.g., a sidewall of the first detent opening 61) to prevent movement of the first member 48 when the detent 62 is in the first position. The detent 62 may be disengaged from (e.g., flexed radially inwardly) the housing 32 when the detent 62 is in the second position.

Figure 16:
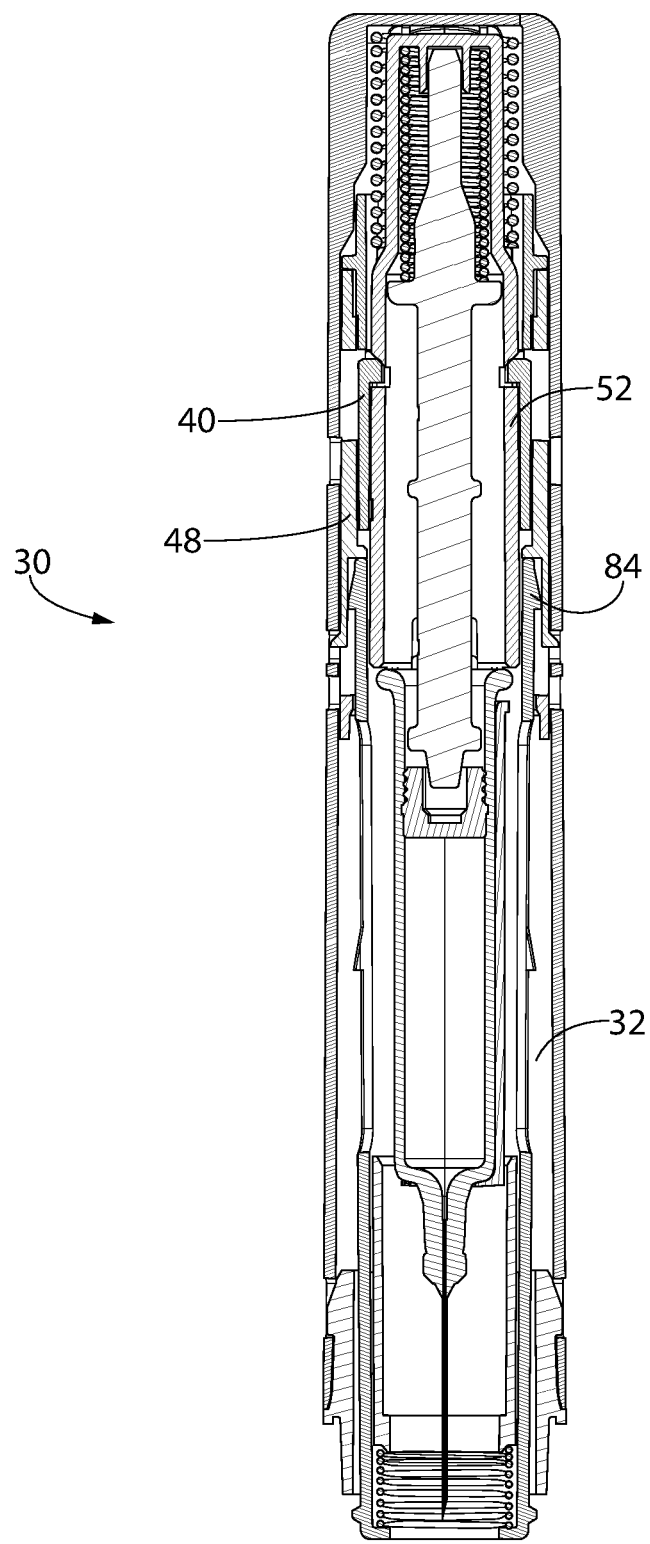
FIG. 16 is a sectional view of the injector of FIG. 1 with the needle guard in a retracted configuration.
Figure 17:
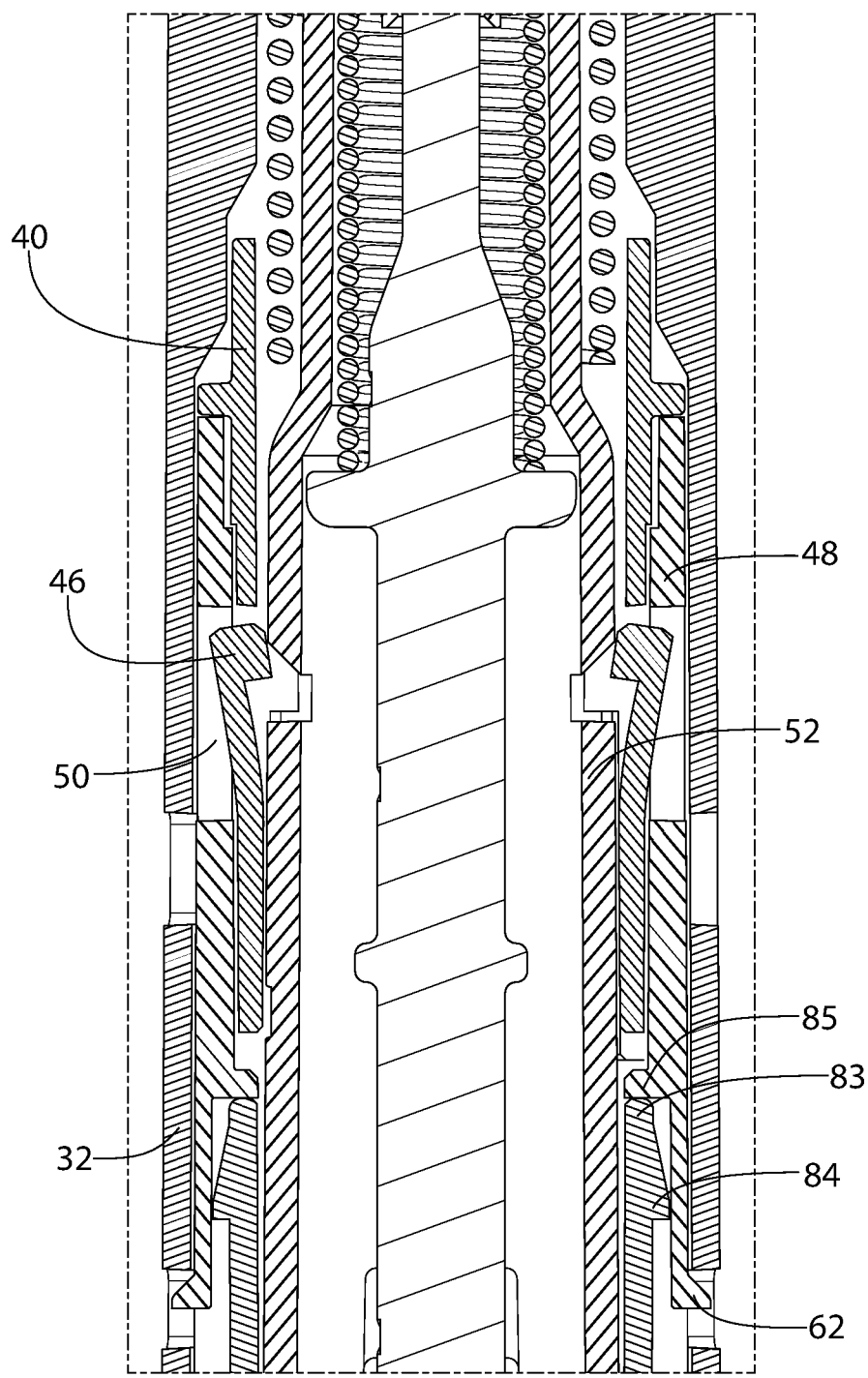
FIG. 17 is a close-up view of a portion of the sectional view of FIG. 16.

Referring to FIGS. 16-17, the engagement surface 83 of the leg 82 may contact a ledge 85 of the first member 48 as a user pushes the distal end of the needle guard 78 against an injection site and the needle guard 78 moves relative to the housing 32 from the extended position toward the retracted position. In some embodiments, the user sets a triggering sequence into motion by moving the needle guard 78 relative to the housing 32. In some embodiments, the needle guard 78 is the trigger that activates the injector 30. In some embodiments, movement of the needle guard 78 triggers the injector 30 to deliver a dose of medicament to a user. The needle guard protrusion 84 may move along a length of the detent 62 of the first member 48 as the needle guard 78 moves relative to the housing 32. The needle guard protrusion 84 may no longer block movement of the detent 62 when the engagement surface 83 contacts the ledge 85 such that the detent 62 can move from the first position to the second position.

Referring to FIGS. 16-17 the needle guard 78 may move the second member 40 as the needle guard 78 continues to move proximally after the engagement surface 83 contacts the engagement surface 85. Proximal movement of the needle guard 78 may move the second member 40 proximally. The detent 62 of the first member 48 may move from the first detent opening 61 to the second detent opening 63 as the second member 40 moves proximally relative to the housing 32. The detent 62 may be moveable between a first position, a second position, and a third position. The detent 62 may be within the first detent opening 61 in the first position. The detent may be removed from the first detent opening 61 in the second position. The detent 62 may be within the second detent opening 63 in the third position. The first arm 46 of the second member 40 may be aligned with the opening 50 of the first member 48 when the first member 48 is moved proximally relative to the housing 32. The first arm 46 may move out of the first recess 54 of the shell 52 when the opening 50 is aligned with the first arm 46.

Referring to FIGS. 18-19, the first biasing element 56 may move the shell 52 when the first arm 46 disengages from the first recess 54 of the shell 52. The first biasing element 56 may move the shell 52 distally. The first biasing element 56 may move the shell 52 relative to the housing 32 from the initial position to the injecting position when the first member 48 moves with respect to the housing 32. Proximal movement of the needle guard 78 and the first member 48 may cause distal movement of the shell 52. The shell 52, ram 58, syringe 72, and syringe holder 98 may move distally relative to the housing 32 as the first biasing element 56 moves the shell 52. The needle 74 may extend through the opening 92 of the needle guard 78 as the shell 52 moves to the injecting position.

Referring to FIG. 20, the injector 30 may have an insertion depth defined by the length of the needle 74 that extends through the opening 92 of the needle guard 78. In some embodiments, the insertion depth of the needle 74 is about 5 mm, about 10 mm, about 15 mm, about 16 mm, about 20 mm, about 25 mm, about 30 mm, about 35 mm, about 40 mm, about 45 mm, or about 50 mm. In some embodiments, the insertion depth of the needle 74 is about 5 mm to about 10 mm, about 10 mm to about 15 mm, about 15 mm to about 20 mm, about 20 mm to about 25 mm, about 25 mm to about 30 mm, about 30 mm to about 35 mm, about 35 mm to about 40 mm, about 40 mm to about 45 mm, or about 45 mm to about 50 mm. In some embodiments, the needle guard is configured to travel about 1 mm, about 2 mm, about 3 mm, about 4 mm, about 5 mm, about 6 mm, mm, about 7 mm, about 8 mm, about 9 mm, about 10 mm, about 11 mm, about 12 mm, about 13 mm, about 14 mm, or about 15 mm. In one embodiment, the needle may extend approximately 20 mm to about 25 mm from the distal end of the needle guard 78 in response to travel of the needle guard of approximately 1 mm to about 5 mm or about 5 mm to about 10 mm. The insertion depth may be independent of the length of travel of the needle guard 78. The shell 52 may move distally until the end wall 104 on the syringe holder 98 engages a rim 128 of the collar 38 (FIG. 20). The shell 52 may be in the injecting position when the syringe holder 98 engages the rim 128 of the collar. In some embodiments, the position of the ram 58 relative to the syringe 72 is fixed such that no medicament is ejected as the shell 52 moves toward the distal end of the injector 30. In other embodiments, the ram 58 may begin to move relative to the syringe 72 prior to the syringe holder 98 engaging the rim 128.

Figure 21:
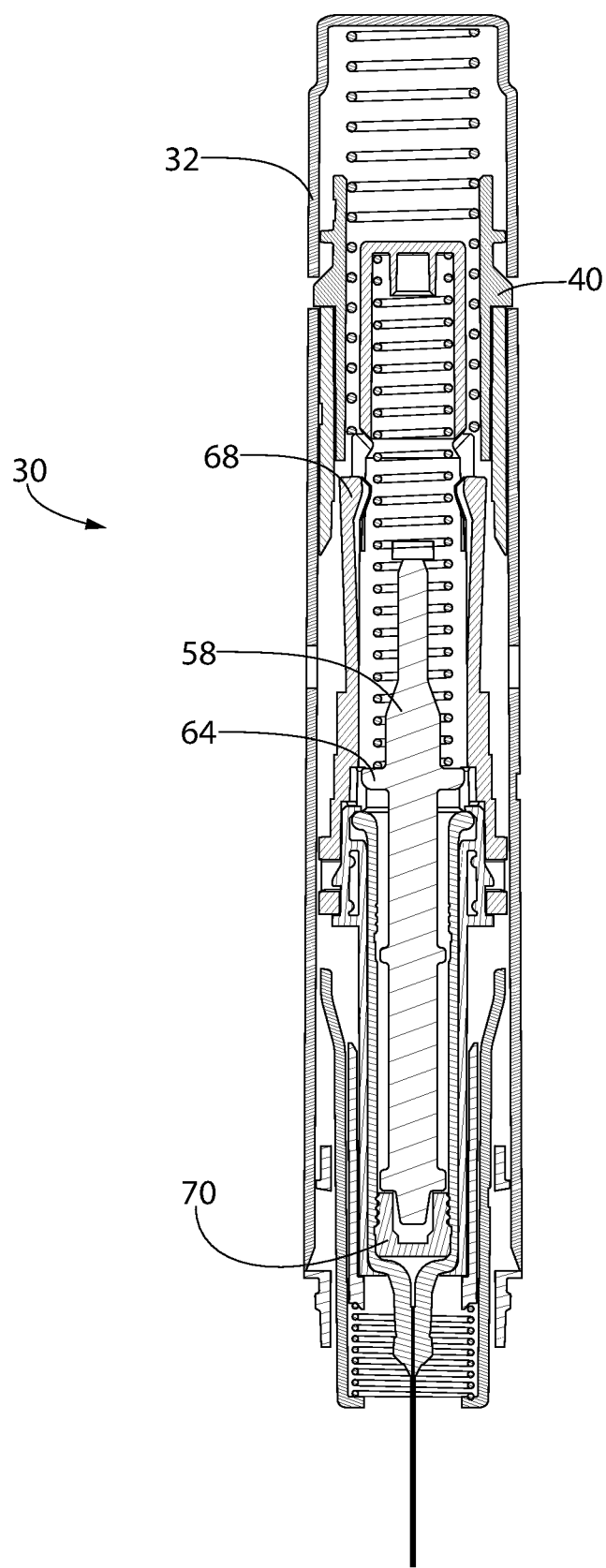
FIG. 21 is a sectional view of the injector of FIG. 1 with the shell in an injecting position.
Figure 22:
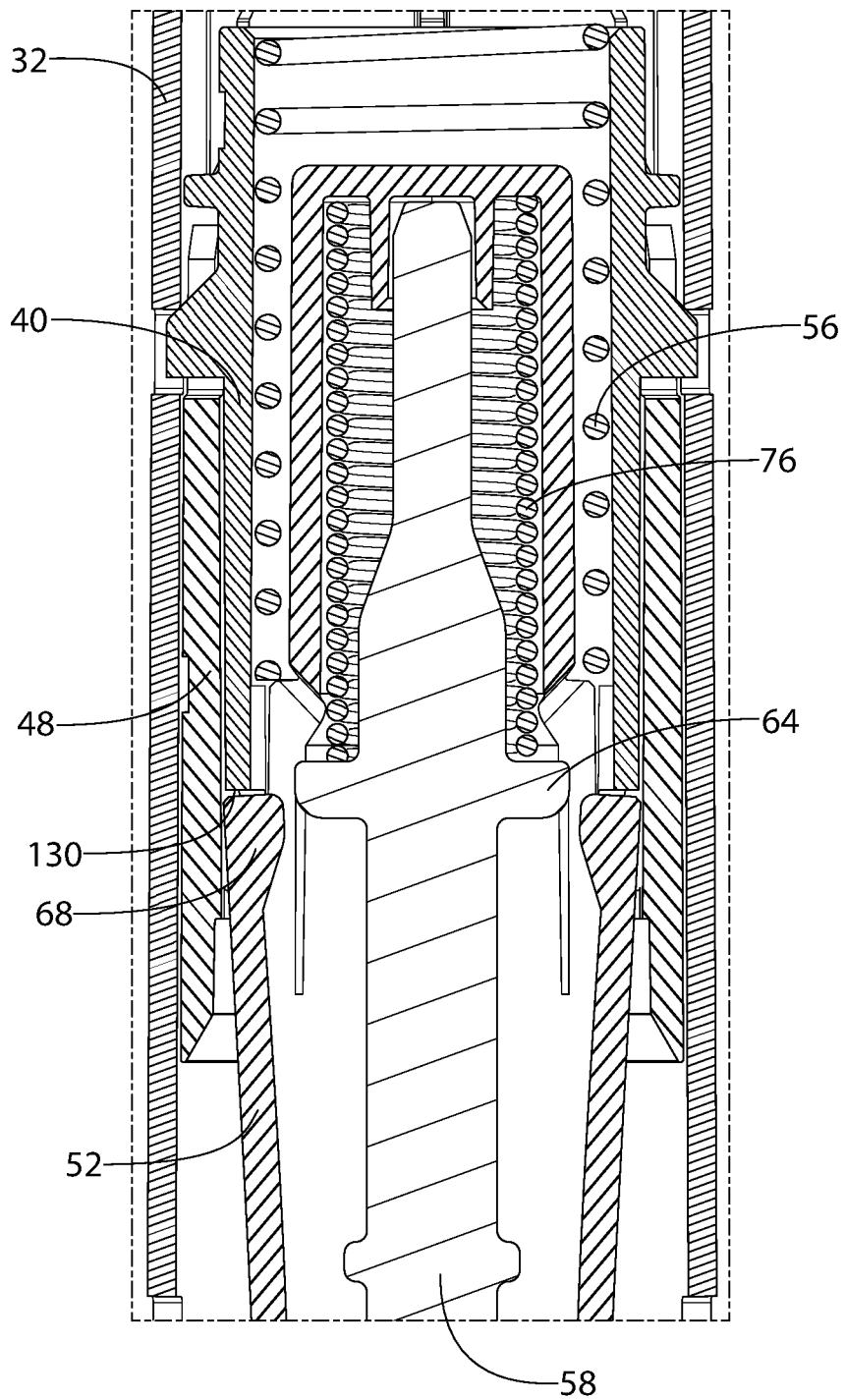
FIG. 22 is a close-up view of a portion of the sectional view of FIG. 21.

Referring to FIGS. 21-22, the engagement member 68 of the shell 52 may be positioned distally of the second member 40 when the shell 52 is in the injecting position. The engagement member 68 may move radially outwardly when the engagement member 68 moves beyond the second member 40. The movement of the engagement member 68 may disengage the engagement member 68 from the rim 64 of the ram 58. The second biasing element 76 may move the ram 58 toward the distal end of the injector 30 when the rim 64 is no longer engages engagement member 68. The engagement member 68 may be moveable from a restrained configuration to an expanded configuration. The engagement member 68 may be in the restrained configuration when the engagement member 68 is within a recess defined by the second member 40. The engagement member 68 may move radially outwardly to the expanded configuration when the engagement member 68 clears a distal end 130 of the second member 40 and the engagement member 68 is no longer confined by the second member 40. The engagement member 68 may not be in contact with the rim 64 or may allow distal movement of the ram 58 when the engagement member 68 is in the expanded configuration. In some embodiments, the second biasing element 76 does not begin to expand until the shell 52 is in the injecting position.

Referring to FIG. 22, the second biasing element 76 may apply a force to the rim 64 of the ram 58 to move the ram distally. The second biasing element 76 may move the ram 58 when the engagement member 68 of the shell 52 is in the expanded configuration. The ram 58 may move the plunger 70 to dispense medicament from the syringe 72, through the needle 74 and into the user or patient. In some embodiments, the ram 58 is spaced from the plunger 70 prior to movement of the ram 58. In other embodiments, the ram 58 is associated with (e.g., in contact or close proximity with) the plunger 70 prior to movement of the ram 58. The ram 58 may move the plunger to an end of the syringe 72 to dispense all, a majority of, or a portion of the medicament from the syringe 72.

Figure 23:
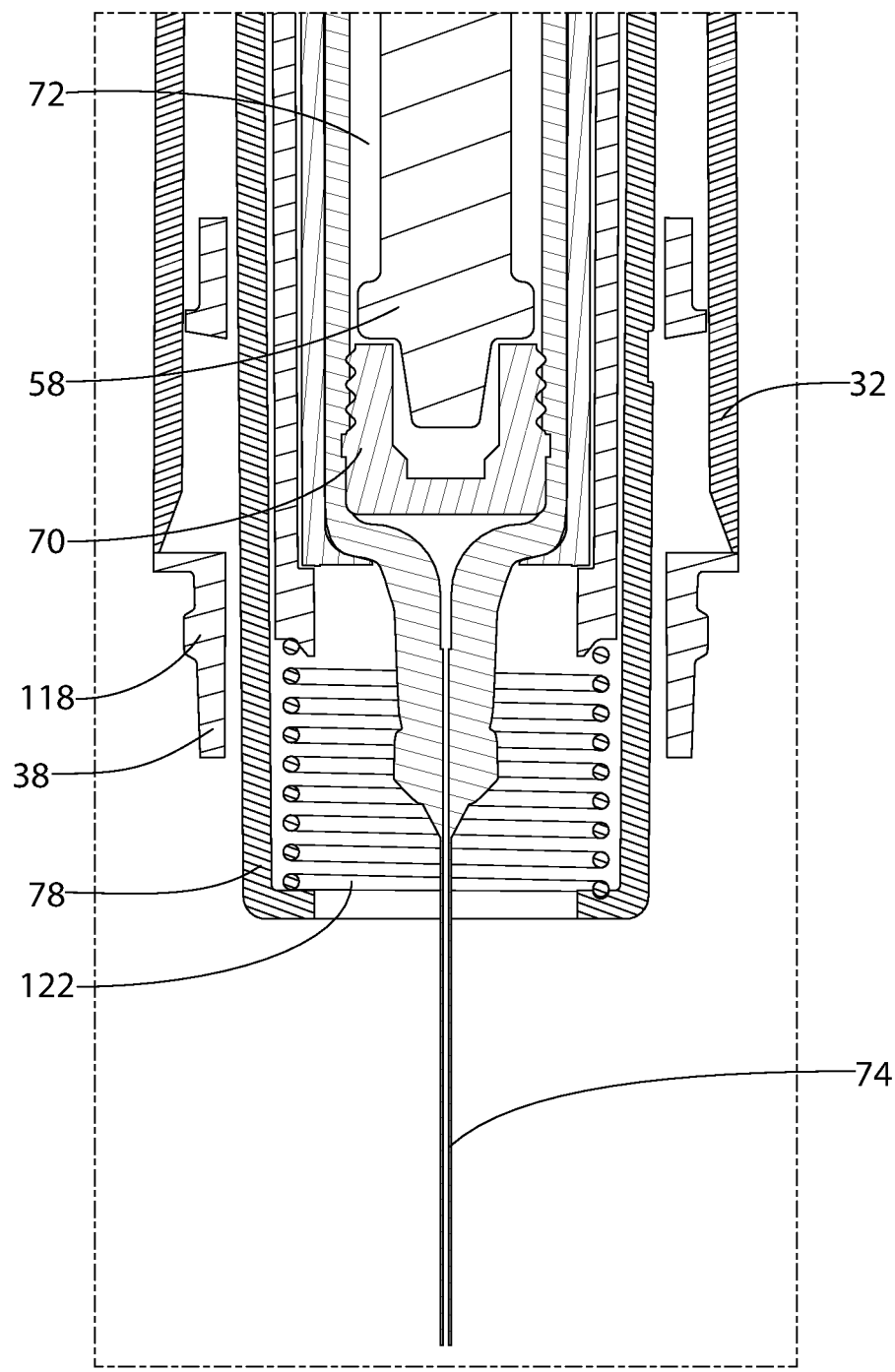
FIG. 23 is a close-up view of a portion of the injector in a fired configuration.

Referring to FIGS. 21 and 23, a third biasing element 122 may be positioned within the needle guard 78. The third biasing element 122 may be operatively associated with the needle guard 78 and the collar 38. The third biasing element 122 may bias the needle guard 78 toward the extended position. The third biasing element 122 may compress as the needle guard 78 is moved proximally relative to the housing 32. The needle guard 78 may be configured to axially translate about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm relative to the housing 32. The needle 74 may still be within the recess defined by the needle guard 78 when the needle guard 78 is initially moved out of the extended configuration (FIG. 16). An end of the needle 74 may be exposed when the needle guard 78 is moved to the retracted position (FIG. 21). The third biasing element 122 may bias the needle guard 78 toward the extended position. In some embodiments, travel of the syringe 72 or syringe carrier 98 is not impeded or cushioned by the third biasing element 122.

Figure 24:
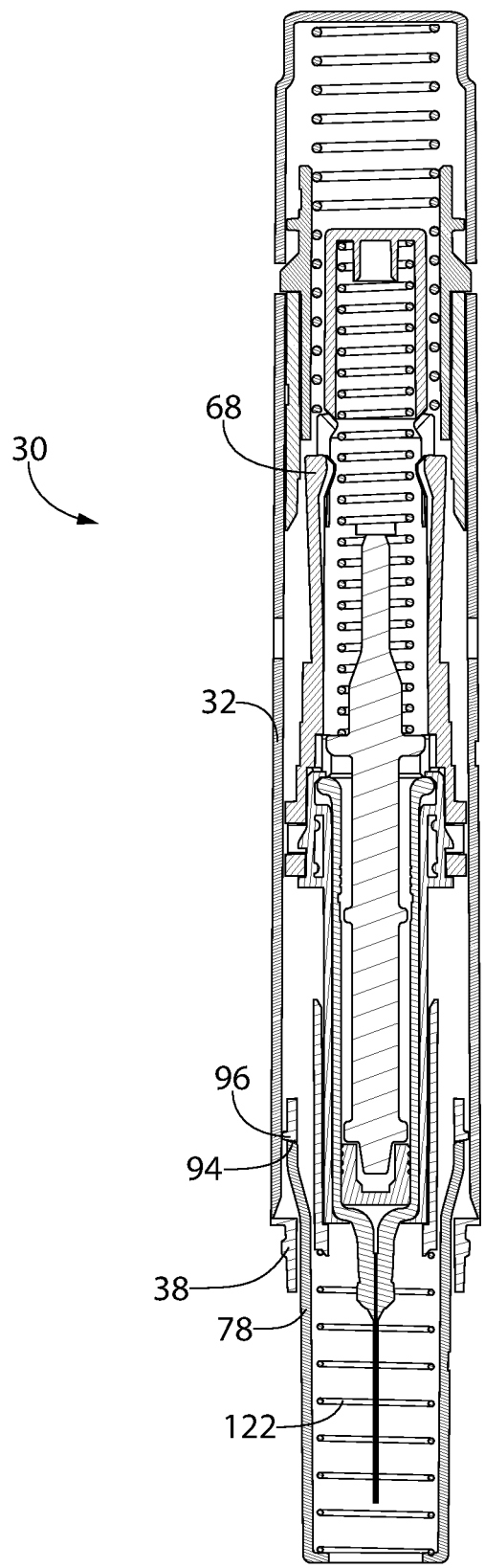
FIG. 24 is a sectional view of the injector of FIG. 1 in a lockout configuration.
Figure 25:
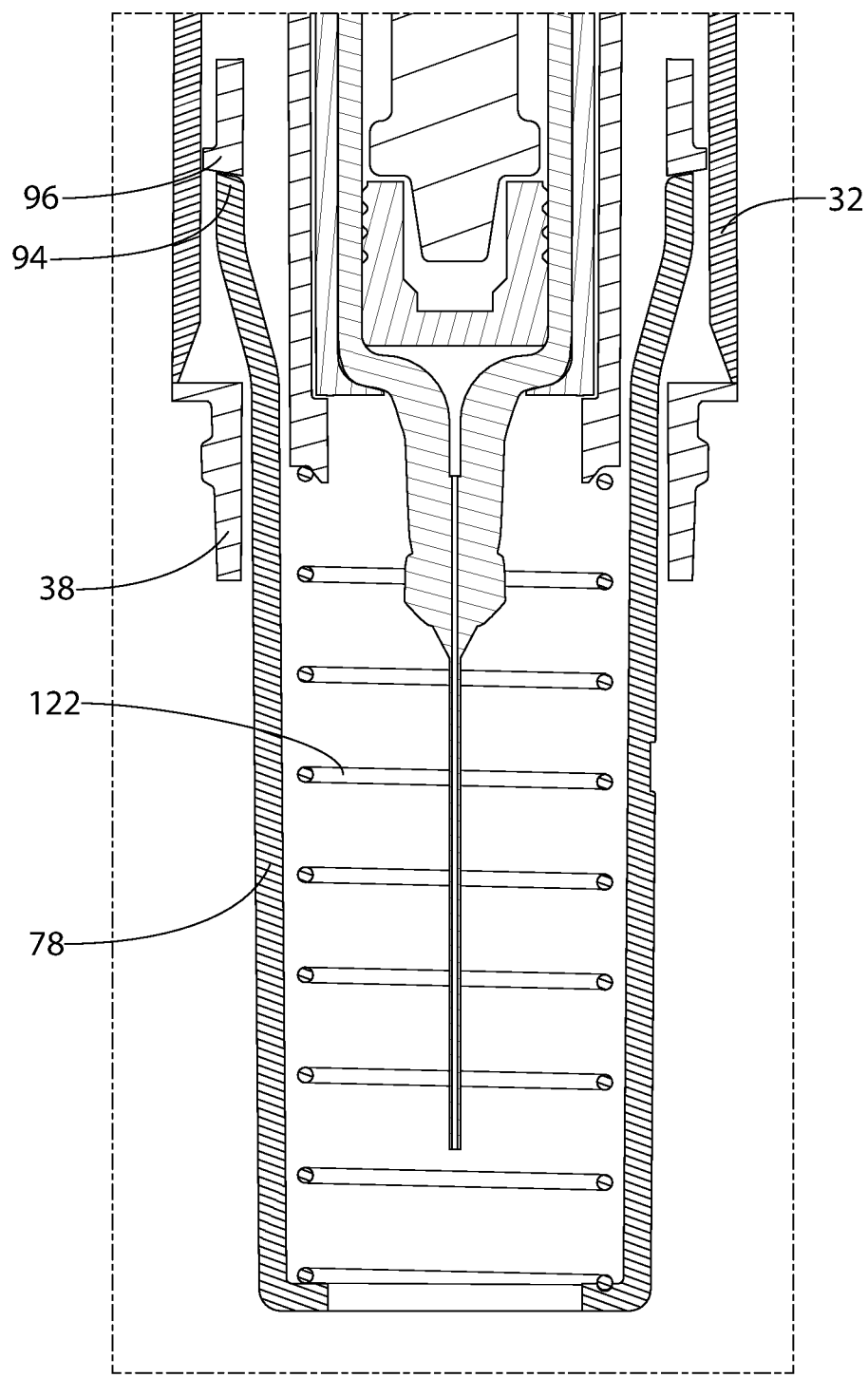
FIG. 25 is a close-up view of a portion of the sectional view of FIG. 24.

Referring to FIGS. 4 and 24-25, the injector 30 may be removed from the injection site after the medicament has been dispensed from the syringe 72. The needle guard 78 may be movable to a lockout position after the injector 30 has been activated and is removed from the injection site. The third biasing element 122 may move the needle guard 78 to the extended lockout position when the needle guard is no longer in contact with the injection site or when the needle guard 78 is no longer being pressed against the injection site. The third biasing element 122 may move the needle guard 78 distally relative to the housing 32. The needle guard 78 may extend away from the housing 32 a greater distance when the needle guard is in the lock out position than when the injector is in the pre-firing, extended position. The needle guard 78 may include a lockout arm 94 configured to lock the needle guard 78 in the lockout position. The lockout arm 94 may prevent proximal movement of the needle guard 78 when the needle guard 78 is in the lockout position. The lockout arm 94 may be biased to flex radially outwardly. The lockout arm 94 may flex radially outwardly such that the lockout arm 94 is positioned in a lockout opening 96 of the collar 38 (FIG. 25) as the needle guard 78 moves to the lockout position. The injector 30 may be in a lockout configuration when the lockout arm 94 is within the lockout opening 96. The lockout arm 94 may be configured to contact a lockout surface or sidewall of the lockout opening 96 such that the needle guard 78 cannot move proximally relative to the housing 32 when the injector 30 is in the lockout configuration.

Figure 26:
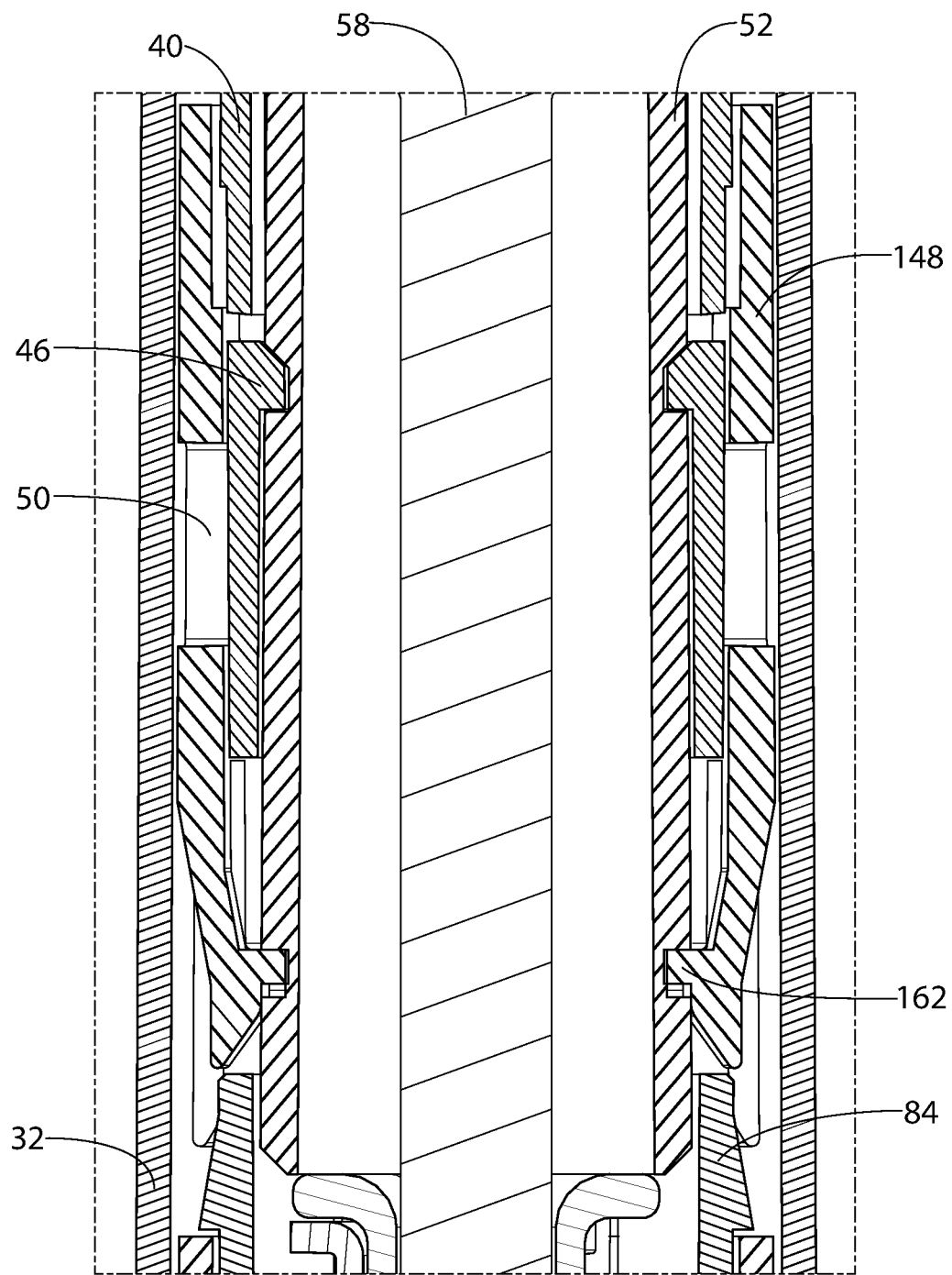
FIG. 26 is a close up sectional view of a second member, first member, and shell in a ready position in accordance with another exemplary embodiment of the present invention.
Figure 27:
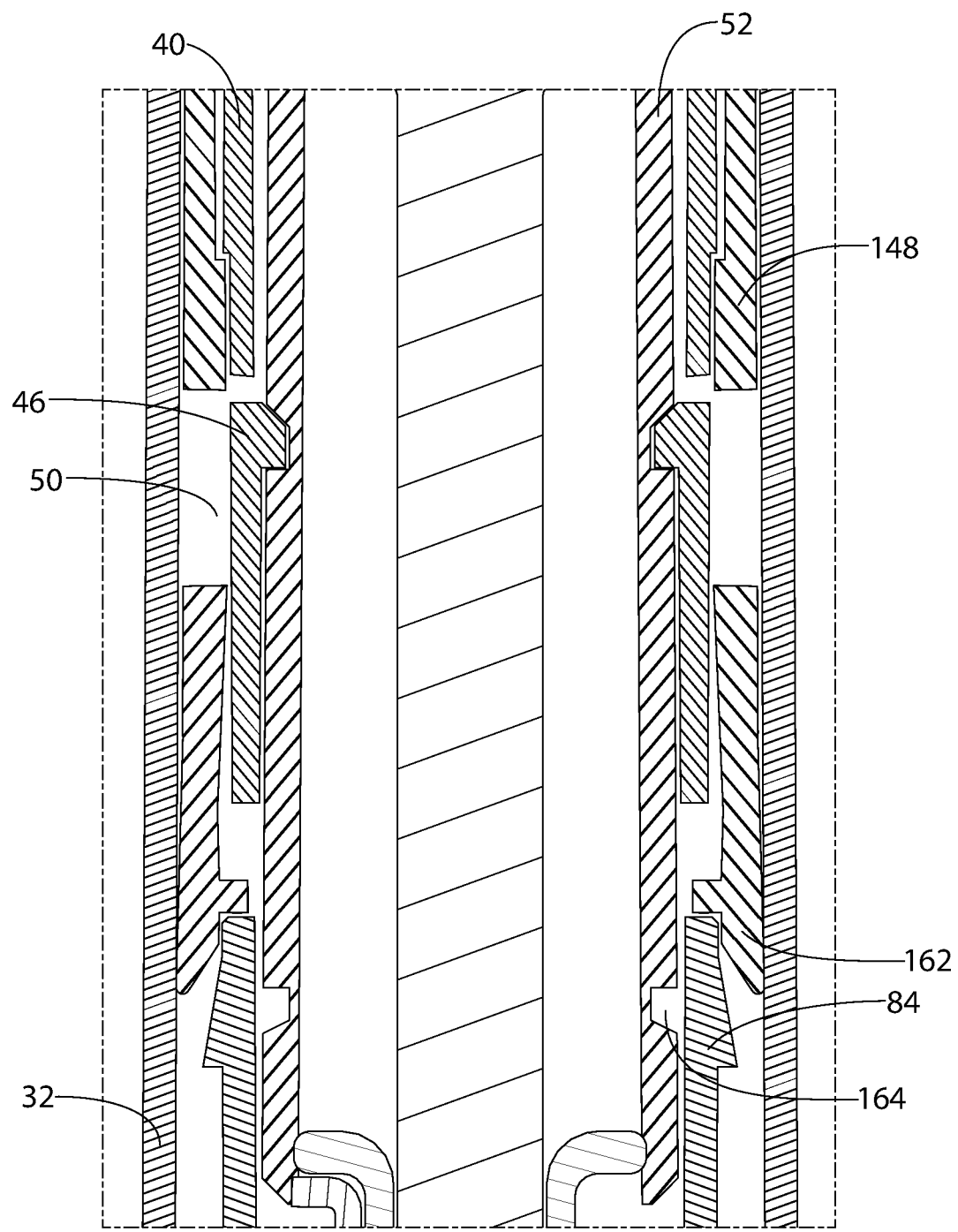
FIG. 27 is a close up of the second member, first member, and shell of FIG. 26 during a transition from the ready position to a firing position.

Referring to FIGS. 26-27, there is shown a second embodiment of the first member 148. The first member 148 may be similar to the first embodiment of the first member 48 except that the detent 162 of first member 148 may engage a recess 164 in the shell 52 when the shell 52 is in the initial position. The needle guard protrusion 84 of the needle guard may engage detent 162 as the needle guard 78 moves with respect to the housing 32. The needle guard protrusion 84 may force the detent 162 to flex radially outwardly as the needle guard 78 moves proximally relative to the housing 32. The detent 162 may disengage from the shell recess 164 when the detent 162 flexes radially outwardly. The needle guard 78 may move the first member 148 proximally relative to the shell 52 and the second member 40. The opening 50 may be aligned with the first arm 46 when the needle guard 78 moves the first member 148 relative to the housing 32 such that the injector 30 may move the shell 52 to the injecting position and deliver a dose of medicament as previously described.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "inwardly" and "outwardly" refer to directions toward and away from, respectively, the geometric center of the injector. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. An injector comprising:
a housing having a proximal end and a distal end;
a medicament chamber containing a medicament;
a shell positioned within the housing and having a cavity to receive at least a portion of the medicament chamber, the shell moveable with respect to the housing from an initial position to an injecting position, the shell including a flexible arm moveable between an engaged position and a disengaged position;
a needle guard including an engagement surface engageable with the flexible arm when the flexible arm is in the engaged position, the needle guard being moveable with respect to the shell when the flexible arm is in the disengaged position, the needle guard moveable between an extended position and a retracted position;
a first member within the housing; and
an actuation assembly coupled to the housing and the shell,
wherein the needle guard moves the first member with respect to the housing as the needle guard moves from the extended position to the retracted position,
wherein the movement of the first member with respect to the housing automatically causes the actuation assembly to move the shell from the initial position to the injecting position,
wherein the actuation assembly moves a plunger with respect to the shell when the shell is in the injecting position and the flexible arm is in the disengaged position,
wherein the first member engages the housing to at least temporarily maintain a position of the first member with respect to the housing, wherein the needle guard disengages the first member from the housing and moves the first member with respect to the housing as the needle guard moves from the extended position to the retracted position, wherein proximal movement of the needle guard moves the first member proximally with respect to the housing, and wherein the shell moves distally with respect to the housing when the first member moves proximally with respect to the housing.

2. The injector of claim 1, wherein the shell moves with respect to the housing in response to the movement of the needle guard.

3. The injector of claim 1, wherein the first member includes a detent moveable from a first position to a second position, wherein the detent engages the housing to prevent the movement of the first member when the detent is in the first position and wherein the detent is disengaged from the housing when the detent is in the second position.

4. The injector of claim 3, wherein the needle guard prevents the movement of the detent from the first position to the second position when the needle guard is in the extended position.

5. The injector of claim 1, further comprising:
a second member fixed to the housing, the second member including a catch engageable with the shell to prevent the movement of the shell with respect to the housing.

6. The injector of claim 5, wherein the second member at least partially encircles the shell.

7. The injector of claim 5, wherein the shell includes a recess and the catch is positioned within the recess when the catch is in a first position.

8. The injector of claim 7, wherein the catch moves out of the recess when the first member moves with respect to the housing.

9. The injector of claim 1, wherein the actuation assembly includes a first biasing element operatively associated with the housing and the shell, wherein the first biasing element moves the shell relative to the housing from the initial position to the injecting position when the first member moves with respect to the housing.

10. The injector of claim 9, wherein the actuation assembly includes a second biasing element operatively associated with the shell and the plunger, wherein the second biasing element moves the plunger with respect to the shell when the shell is in the injecting position.

11. The injector of claim 1, wherein the flexible arm is in the engaged position when the shell is in the initial position and the flexible arm is in the disengaged position when the shell is in the injecting position.

12. The injector of claim 11, further comprising:
a second member fixed to the housing, the second member including a catch engageable with the shell to prevent the movement of the shell with respect to the housing, wherein the second member blocks the movement of the flexible arm from the engaged position to the disengaged position when the shell is in the initial position.

13. The injector of claim 1, further comprising:
a syringe; and
a syringe holder having a first end, a second end, a longitudinal axis extending from the first end to the second end, and a sidewall extending from the first end toward the second end, the sidewall defining a receiving area for the syringe, wherein the sidewall includes a sidewall opening such that the syringe can be loaded into the syringe holder from a side of the syringe holder.

14. The injector of claim 13, wherein the syringe is loaded into the syringe holder without moving axially through a rear opening of the syringe holder.

15. The injector of claim 13, wherein a needle shield is coupled to the syringe and the syringe is loaded into the syringe holder without passing the needle shield through the syringe holder.

16. The injector of claim 13, wherein the sidewall opening extends from the first end to the second end.

17. The injector of claim 13, wherein the syringe includes a body defining the medicament chamber, a needle fluidly coupled to the medicament chamber, and a needle shield that receives the needle, the needle shield having a needle shield diameter, and
wherein the syringe holder includes an end wall having an end wall opening with an end wall opening diameter that is smaller than the needle shield diameter.

18. The injector of claim 17, wherein the syringe includes a syringe flange at a proximal end of the syringe, wherein a distal end of the syringe engages the end wall and the syringe flange is spaced from a second end of the sidewall when the syringe is coupled to the syringe holder.

19. The injector of claim 17, further comprising:
a needle shield remover having a projection positioned between a proximal end of the needle shield and a distal end of the syringe.

20. The injector of claim 19, further comprising:
a cap coupled to the housing, the needle shield remover coupled to the cap such that the needle shield is removed when the cap is decoupled from the housing.

21. The injector of claim 20, wherein the cap at least temporarily maintains the needle guard in the extended position.

22. The injector of claim 17, wherein the movement of the plunger expels the medicament from the medicament chamber through the needle.

23. The injector of claim 13, wherein the syringe includes a body defining the medicament chamber, a needle fluidly coupled to the medicament chamber, and a needle shield that receives the needle, the needle shield having a needle shield diameter, and
wherein the syringe holder includes an end wall having an end wall opening with an end wall opening diameter that is larger than the needle shield diameter.

24. The injector of claim 1, wherein the needle guard is moveable to a lockout position and the needle guard includes a needle guard lock that engages a lockout surface to prevent proximal movement of the needle guard when the needle guard is in the lockout position.

25. The injector of claim 24, wherein the needle guard lock includes a lockout arm that flexes radially outwardly to engage the lockout surface when the needle guard is in the lockout position.

26. The injector of claim 24, further comprising:
a collar coupled to the housing, the collar including the lockout surface.

27. The injector of claim 26, further comprising:
a biasing element coupled to the collar and the needle guard, the biasing element biasing the needle guard toward the extended position.

28. The injector of claim 1, wherein the medicament comprises diazepam.

29. The injector of claim 1, wherein the medicament comprises testosterone.

* * * * *